(12) United States Patent
Garcia et al.

(10) Patent No.: US 9,512,194 B2
(45) Date of Patent: Dec. 6, 2016

(54) MODIFIED IL-13 POLYPEPTIDES

(71) Applicant: The Board of Trustees of the Leland Stanford Junior University, Palo Alto, CA (US)

(72) Inventors: Kenan Christopher Garcia, Menlo Park, CA (US); Ignacio Moraga Gonzalez, Palo Alto, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 225 days.

(21) Appl. No.: 14/373,498

(22) PCT Filed: Jan. 25, 2013

(86) PCT No.: PCT/US2013/023194
§ 371 (c)(1),
(2) Date: Jul. 21, 2014

(87) PCT Pub. No.: WO2013/112871
PCT Pub. Date: Aug. 1, 2013

(65) Prior Publication Data
US 2015/0056162 A1 Feb. 26, 2015

Related U.S. Application Data

(60) Provisional application No. 61/591,781, filed on Jan. 27, 2012.

(51) Int. Cl.
*C07K 14/54* (2006.01)
*A61K 38/20* (2006.01)

(52) U.S. Cl.
CPC ....... *C07K 14/5437* (2013.01); *A61K 38/2086* (2013.01)

(58) Field of Classification Search
CPC .................. C07K 14/5437; A61K 38/2086
See application file for complete search history.

(56) References Cited

U.S. PATENT DOCUMENTS

| | | |
|---|---|---|
| 2003/0013851 A1 | 1/2003 | Powers et al. |
| 2004/0248260 A1 | 12/2004 | Heavner et al. |
| 2006/0035856 A1 | 2/2006 | Caput et al. |
| 2007/0160658 A1 | 7/2007 | Connor et al. |

FOREIGN PATENT DOCUMENTS

| | | |
|---|---|---|
| WO | 9404680 A1 | 3/1994 |
| WO | 01/25282 A1 | 4/2001 |
| WO | 01/62933 A3 | 8/2001 |
| WO | 02/18422 A1 | 3/2002 |

OTHER PUBLICATIONS

Madhankumar et al., "Interleukin 13 Mutants of Enhanced Avidity Toward the Glioma-Associated Receptor. IL13RALPHA2" Neoplasia, Jan. 1, 2004, pp. 15-22, vol. 6. No. 1, Elsevier, Amsterdam, Netherlands.
Eisenmesser et al., "Solution structure of interleukin-13 and insights into receptor engagement" Journal of Molecular Biology, Jun. 29, 2001, pp. 231-241. vol. 310. No. 1. 29, ASBMB, Rockville, MD.
Thompson et al., "Mutants of Interleukin 13 With Altered Reactivity Toward Interleukin 13 Receptors" Journal of Biological Chemistry, Oct. 1999, pp. 29944-29950, vol. 274. No. 42. 15 ASBMB, Rockville, MD.
Corren; et al., "Lebrikizumab treatment in adults with asthma.", N Engl J Med (Sep. 2011) 365(12):1088-98.
Eisenmesser; et al., "Solution structure of interleukin-13 and insights into receptor engagement.", J Mol Biol. (Jun. 2001), 310(1):231-41.
Ito; et al., "Distinct structural requirements for interleukin-4 (IL-4) and IL-13 binding to the shared IL-13 receptor facilitate cellular tuning of cytokine responsiveness.", J Biol Chem (Sep. 2009), 284(36):24289-96.
Madhankumar; et al., "Interleukin 13 mutants of enhanced avidity toward the glioma-associated receptor, IL13Ralpha2.", Neoplasia (Jan.-Feb. 2004), 6(1):15-22.
Oshima; et al., "Conversion of interleukin-13 into a high affinity agonist by a single amino acid substitution.", J Biol Chem (May 2000), 275(19):14375-80.
Oshima; et al., "Characterization of a powerful high affinity antagonist that inhibits biological activities of human interleukin-13.", J Biol Chem (May 2001), 276(18):15185-91.
Partaledis; et al., "In vitro selection and characterization of human immunodeficiency virus type 1 (HIV-1) isolates with reduced sensitivity to hydroxyethylamino sulfonamide inhibitors of HIV-1 aspartyl protease.", J Virol. (Sep. 1995), 69(9):5228-35.
Thompson; et al., "Mutants of interleukin 13 with altered reactivity toward interleukin 13 receptors.", J Biol CHem (Oct. 1999), 274(42):29944-50.

*Primary Examiner* — Prema Mertz
(74) *Attorney, Agent, or Firm* — Pamela J. Sherwood; Bozicevic, Field & Francis LLP

(57) ABSTRACT

Variant IL-13 polypeptides are provided, which are engineered to have one or more of the following properties: (a) altered affinity for IL-13Rα2, relative to the native human IL-13 protein; (b) altered affinity for IL-13Rα1 relative to the native human IL-13 protein; (c) a disruption in the binding site for IL-4Rα relative to the native human IL-13 protein.

7 Claims, 8 Drawing Sheets

SEQUENCE LISTING

```
<160> NUMBER OF SEQ ID NOS: 20

<210> SEQ ID NO 1
<211> LENGTH: 113
<212> TYPE: PRT
<213> ORGANISM: Homo sapiens

<400> SEQUENCE: 1

Pro Gly Pro Val Pro Pro Ser Thr Ala Leu Arg Glu Leu Ile Glu Glu
1               5                   10                  15

Leu Val Asn Ile Thr Gln Asn Gln Lys Ala Pro Leu Cys Asn Gly Ser
            20                  25                  30

Met Val Trp Ser Ile Asn Leu Thr Ala Gly Met Tyr Cys Ala Ala Leu
        35                  40                  45

Glu Ser Leu Ile Asn Val Ser Gly Cys Ser Ala Ile Glu Lys Thr Gln
    50                  55                  60

Arg Met Leu Ser Gly Phe Cys Pro His Lys Val Ser Ala Gly Gln Phe
65                  70                  75                  80

Ser Ser Leu His Val Arg Asp Thr Lys Ile Glu Val Ala Gln Phe Val
                85                  90                  95
```

Lys Asp Leu Leu Leu His Leu Lys Lys Leu Phe Arg Glu Gly Gln Phe
            100                 105                 110

Asn

<210> SEQ ID NO 2
<211> LENGTH: 113
<212> TYPE: PRT
<213> ORGANISM: Homo sapiens

<400> SEQUENCE: 2

Pro Gly Pro Val Pro Pro Ser Thr Ala Val Arg Ala Leu Ile Glu Glu
1               5                   10                  15

Leu Ile Asn Ile Thr Gln Asn Gln Lys Ala Pro Leu Cys Asn Gly Ser
            20                  25                  30

Met Val Trp Ser Ile Asn Arg Thr Ala Gly Met Tyr Cys Ala Ala Leu
        35                  40                  45

Glu Ser Leu Ile Asn Val Ser Gly Cys Ser Ala Ile Glu Lys Thr Gln
    50                  55                  60

Asp Met Leu Ser Gly Phe Cys Pro His Lys Val Ser Ala Gly Gln Phe
65                  70                  75                  80

Ser Ser Leu His Val Arg Ser Ser Lys Ile Glu Val Ala Gln Phe Val
                85                  90                  95

Lys Asp Leu Leu Phe His Leu Arg Thr Leu Phe Arg Glu Gly Gln Phe
            100                 105                 110

Asn

<210> SEQ ID NO 3
<211> LENGTH: 113
<212> TYPE: PRT
<213> ORGANISM: Homo sapiens

<400> SEQUENCE: 3

Pro Gly Pro Val Pro Pro Ser Thr Ala Ile Arg Glu Leu Ile Glu Glu
1               5                   10                  15

Leu Ile Asn Ile Thr Gln Asn Gln Lys Ala Pro Leu Cys Asn Gly Ser
            20                  25                  30

Met Val Trp Ser Ile Asn Leu Thr Ala Gly Met Tyr Cys Ala Ala Leu
        35                  40                  45

Glu Ser Leu Ile Asn Val Ser Gly Cys Ser Ala Ile Glu Lys Thr Gln
    50                  55                  60

Arg Met Leu Ser Gly Phe Cys Pro His Lys Val Ser Ala Gly Gln Phe
65                  70                  75                  80

Ser Ser Leu His Val Arg Gly Ser Lys Ile Glu Val Ala Gln Phe Val
                85                  90                  95

Lys Asp Leu Leu His His Leu Arg Ala Leu Phe Arg Glu Gly Gln Phe
            100                 105                 110

Asn

<210> SEQ ID NO 4
<211> LENGTH: 113
<212> TYPE: PRT
<213> ORGANISM: Homo sapiens

```
<400> SEQUENCE: 4

Pro Gly Pro Val Pro Ser Thr Ala Val Arg Glu Leu Ile Glu Glu
1               5                   10                  15

Leu Ile Asn Ile Thr Gln Asn Gln Lys Ala Pro Leu Cys Asn Gly Ser
            20                  25                  30

Met Val Trp Ser Ile Asn Arg Thr Ala Gly Met Tyr Cys Ala Ala Leu
        35                  40                  45

Glu Ser Leu Ile Asn Val Ser Gly Cys Ser Ala Ile Glu Lys Thr Gln
    50                  55                  60

Arg Met Leu Ser Gly Phe Cys Pro His Lys Val Ser Ala Gly Gln Phe
65                  70                  75                  80

Ser Ser Leu His Val Arg Ser Ser Lys Ile Glu Val Ala Gln Phe Val
                85                  90                  95

Lys Asp Leu Leu Phe His Leu Arg Thr Leu Phe Arg Glu Gly Gln Phe
            100                 105                 110

Asn

<210> SEQ ID NO 5
<211> LENGTH: 113
<212> TYPE: PRT
<213> ORGANISM: Homo sapiens

<400> SEQUENCE: 5

Pro Gly Pro Val Pro Ser Thr Ala Leu Ile Glu Leu Ile Glu Glu
1               5                   10                  15

Leu Ile Asn Ile Thr Gln Asn Gln Lys Ala Pro Leu Cys Asn Gly Ser
            20                  25                  30

Met Val Trp Ser Ile Asn Leu Thr Ala Gly Ile Tyr Cys Ala Ala Leu
        35                  40                  45

Glu Ser Leu Ile Asn Val Ser Gly Cys Ser Ala Ile Glu Lys Thr Gln
    50                  55                  60

Arg Met Leu Ser Gly Phe Cys Pro His Lys Val Ser Ala Gly Gln Phe
65                  70                  75                  80

Ser Ser Leu His Val Lys Gly Ser Lys Ile Glu Val Ala Gln Phe Val
                85                  90                  95

Lys Asp Leu Leu His His Leu Arg Ala Leu Met Arg Glu Gly Gln Phe
            100                 105                 110

Asn

<210> SEQ ID NO 6
<211> LENGTH: 113
<212> TYPE: PRT
<213> ORGANISM: Homo sapiens

<400> SEQUENCE: 6

Pro Gly Pro Val Pro Ser Thr Ala Ile Arg Glu Leu Ile Glu Glu
1               5                   10                  15

Leu Leu Asn Ile Thr Gln Asn Gln Lys Ala Pro Leu Cys Asn Gly Ser
            20                  25                  30

Met Val Trp Ser Ile Asn Leu Thr Ala Gly Met Tyr Cys Ala Ala Leu
        35                  40                  45

Glu Ser Leu Ile Asn Val Ser Gly Cys Ser Ala Ile Glu Lys Thr Gln
    50                  55                  60

Arg Met Leu Ser Gly Phe Cys Pro His Lys Val Ser Ala Gly Gln Phe
65                  70                  75                  80
```

```
Ser Ser Leu His Val Met Lys Ser Lys Ile Glu Val Ala Gln Phe Val
                85                  90                  95

Lys Asp Leu Leu His His Leu Arg Ala Leu Phe Arg Glu Gly Gln Phe
            100                 105                 110

Asn

<210> SEQ ID NO 7
<211> LENGTH: 113
<212> TYPE: PRT
<213> ORGANISM: Homo sapiens

<400> SEQUENCE: 7

Pro Gly Pro Val Pro Pro Ser Thr Ala Ile Arg Glu Leu Ile Glu Glu
  1               5                  10                  15

Leu Ile Asn Ile Thr Gln Asn Gln Lys Ala Pro Leu Cys Asn Gly Ser
                20                  25                  30

Met Val Trp Ser Ile Asn Leu Thr Ala Gly Met Tyr Cys Ala Ala Leu
            35                  40                  45

Glu Ser Leu Ile Asn Val Ser Gly Cys Ser Ala Ile Glu Lys Thr Gln
 50                  55                  60

Arg Met Leu Ser Gly Phe Cys Pro His Lys Val Ser Ala Gly Gln Phe
65                  70                  75                  80

Ser Ser Leu His Val Arg Ser Ser Arg Ile Glu Val Ala Gln Phe Val
                85                  90                  95

Lys Asp Leu Leu His His Leu Arg Thr Leu Phe Arg Glu Gly Gln Phe
            100                 105                 110

Asn

<210> SEQ ID NO 8
<211> LENGTH: 113
<212> TYPE: PRT
<213> ORGANISM: Homo sapiens

<400> SEQUENCE: 8

Pro Gly Pro Val Pro Pro Ser Thr Ala Leu Arg Glu Leu Ile Glu Glu
  1               5                  10                  15

Leu Ile Asn Ile Thr Gln Asn Glu Lys Ala Pro Leu Cys Asn Gly Ser
                20                  25                  30

Met Val Trp Ser Ile Asn Leu Thr Ala Gly Ile Tyr Cys Ala Ala Leu
            35                  40                  45

Glu Ser Leu Ile Asn Val Ser Gly Cys Ser Ala Ile Glu Lys Thr Gln
 50                  55                  60

Arg Met Leu Ser Gly Phe Cys Pro His Lys Val Ser Ala Gly Gln Phe
65                  70                  75                  80

Ser Ser Leu His Val Thr Gly Ser Lys Ile Glu Val Ala Gln Phe Val
                85                  90                  95

Lys Asp Leu Leu Tyr His Leu Arg Ala Leu Phe Arg Glu Gly Gln Phe
            100                 105                 110

Asn

<210> SEQ ID NO 9
<211> LENGTH: 113
<212> TYPE: PRT
<213> ORGANISM: Homo sapiens
```

```
<400> SEQUENCE: 9

Pro Gly Pro Val Pro Ser Thr Ala Leu Ser Glu Leu Ile Glu Glu
 1               5                  10                  15

Leu Ile Asn Ile Thr Gln Asn Gln Lys Ala Pro Leu Cys Asn Gly Ser
            20                  25                  30

Met Val Trp Ser Ile Asn Pro Thr Ala Gly Met Tyr Cys Ala Ala Leu
        35                  40                  45

Glu Ser Leu Ile Asn Val Ser Gly Cys Ser Ala Ile Glu Lys Thr Gln
    50                  55                  60

Arg Met Leu Ser Gly Phe Cys Pro His Lys Val Ala Ala Gly Gln Phe
65                  70                  75                  80

Ser Ser Leu His Asp Lys Gly Ser Met Ile Glu Val Ala Gln Phe Val
                85                  90                  95

Lys Asp Leu Leu Tyr His Leu Arg Thr Leu Phe Arg Glu Gly Gln Phe
            100                 105                 110

Asn

<210> SEQ ID NO 10
<211> LENGTH: 113
<212> TYPE: PRT
<213> ORGANISM: Homo sapiens

<400> SEQUENCE: 10

Pro Gly Pro Val Pro Ser Thr Ala Thr Arg Glu Leu Ile Glu Glu
 1               5                  10                  15

Leu Ile Asn Ile Thr Gln Asn Gln Lys Ala Pro Leu Cys Asn Gly Ser
            20                  25                  30

Met Val Trp Ser Ile Asn Leu Thr Ala Asp Met Tyr Cys Ala Ala Leu
        35                  40                  45

Glu Ser Leu Ile Asn Val Ser Gly Cys Ser Ala Ile Glu Lys Thr Gln
    50                  55                  60

Arg Met Leu Ser Gly Phe Cys Pro His Lys Val Ser Val Gly Gln Phe
65                  70                  75                  80

Ser Ser Leu His Val Arg Gly Ser Lys Ile Glu Val Ala Gln Phe Val
                85                  90                  95

Lys Asp Leu Leu Tyr His Leu Arg Thr Leu Phe Arg Glu Gly Gln Phe
            100                 105                 110

Asn

<210> SEQ ID NO 11
<211> LENGTH: 113
<212> TYPE: PRT
<213> ORGANISM: Homo sapiens

<400> SEQUENCE: 11

Pro Gly Pro Val Pro Ser Thr Ala Asp Ile Glu Leu Ile Ala Glu
 1               5                  10                  15

Leu Ile Asn Ile Thr Gln Asn Gln Lys Ala Pro Leu Cys Asn Gly Ser
            20                  25                  30

Met Val Trp Ser Ile Asn Leu Thr Ala Asp Met Tyr Cys Ala Ala Leu
        35                  40                  45

Glu Ser Leu Ile Asn Val Ser Gly Cys Ser Ala Ile Glu Lys Thr Gln
    50                  55                  60

Arg Met Leu Ser Gly Phe Cys Pro His Lys Val Ser Ala Gly Gln Phe
65                  70                  75                  80
```

Ser Ser Leu His Val Lys Lys Thr Arg Ile Glu Val Ala Gln Phe Val
                85                  90                  95

Lys Asp Leu Leu Leu His Leu Lys Lys Leu Phe Lys Glu Gly Gln Phe
            100                 105                 110

Asn

<210> SEQ ID NO 12
<211> LENGTH: 113
<212> TYPE: PRT
<213> ORGANISM: Homo sapiens

<400> SEQUENCE: 12

Pro Gly Pro Val Pro Pro Ser Thr Ala Ala Arg Glu Leu Ile Glu Glu
1               5                   10                  15

Leu Val Asn Ile Thr Gln Asn Gln Lys Ala Pro Leu Cys Asn Gly Ser
            20                  25                  30

Met Val Trp Ser Ile Asn Leu Thr Ala Gly Met Tyr Cys Ala Ala Leu
        35                  40                  45

Glu Ser Leu Ile Asn Val Ser Gly Cys Ser Ala Ile Glu Lys Thr Gln
    50                  55                  60

Arg Met Leu Ser Gly Phe Cys Pro His Lys Val Ser Ala Gly Gln Leu
65                  70                  75                  80

Ser Ser Leu His Val Thr Gly Lys Arg Ile Glu Val Ala Gln Phe Val
                85                  90                  95

Lys Asp Leu Leu Asn His Leu Arg Ala Leu Phe Lys Glu Gly Gln Phe
            100                 105                 110

Asn

<210> SEQ ID NO 13
<211> LENGTH: 113
<212> TYPE: PRT
<213> ORGANISM: Homo sapiens

<400> SEQUENCE: 13

Pro Gly Pro Val Pro Pro Ser Thr Ala Val Arg Glu Leu Ile Glu Glu
1               5                   10                  15

Leu Val Asn Ile Thr Gln Asn Gln Lys Ala Pro Leu Cys Asn Gly Ser
            20                  25                  30

Met Val Trp Ser Ile Asn Leu Thr Ala Gly Met Tyr Cys Ala Ala Leu
        35                  40                  45

Glu Ser Leu Ile Asn Val Ser Gly Cys Ser Ala Ile Glu Lys Thr Gln
    50                  55                  60

Arg Met Leu Ser Gly Phe Cys Pro His Lys Val Ser Ala Gly Gln Phe
65                  70                  75                  80

Ser Ser Leu His Val Arg Asp Thr Arg Ile Glu Val Ala Gln Phe Val
                85                  90                  95

Lys Asp Leu Leu Asn His Leu Lys Glu Leu Phe Thr Glu Gly Gln Phe
            100                 105                 110

Asn

<210> SEQ ID NO 14
<211> LENGTH: 113
<212> TYPE: PRT
<213> ORGANISM: Homo sapiens -continued

```
<400> SEQUENCE: 14

Pro Gly Pro Val Pro Ser Thr Ala Leu Ser Glu Leu Met Glu Glu
1               5                   10                  15

Leu Val Asn Ile Thr Gln Asn Gln Lys Ala Pro Leu Cys Asn Gly Ser
            20                  25                  30

Met Val Trp Ser Ile Asn Leu Thr Ala Gly Met Tyr Cys Ala Ala Leu
        35                  40                  45

Glu Ser Leu Ile Asn Val Ser Gly Cys Ser Ala Ile Glu Lys Thr Gln
    50                  55                  60

Arg Met Leu Ser Gly Phe Cys Pro His Lys Val Ser Ala Gly Gln Phe
65              70                  75                  80

Ser Ser Leu His Val Arg Asp Ser Lys Ile Glu Val Ala Gln Phe Val
                85                  90                  95

Lys Asp Leu Leu Asn His Leu Lys Ala Leu Phe Lys Glu Gly Gln Phe
            100                 105                 110

Asn

<210> SEQ ID NO 15
<211> LENGTH: 112
<212> TYPE: PRT
<213> ORGANISM: Homo sapiens

<400> SEQUENCE: 15

Gly Pro Val Pro Pro Ser Thr Ala Phe Arg Glu Leu Ile Glu Glu Leu
1               5                   10                  15

Val Asn Ile Thr Gln Asn Gln Lys Ala Pro Leu Cys Asn Gly Ser Met
            20                  25                  30

Val Trp Ser Ile Asn Leu Thr Ala Gly Met Tyr Cys Ala Ala Leu Glu
        35                  40                  45

Ser Leu Ile Asn Val Ser Gly Cys Ser Ala Ile Glu Lys Thr Gln Arg
    50                  55                  60

Met Leu Ser Gly Phe Cys Pro His Lys Val Ser Pro Gly Gln Phe Ser
65              70                  75                  80

Ser Leu His Val Thr Asn Ser Arg Ile Glu Val Ala Gln Phe Val Lys
                85                  90                  95

Asp Leu Leu Asn His Leu Lys Ala Leu Phe Lys Glu Gly Gln Tyr Asn
            100                 105                 110

<210> SEQ ID NO 16
<211> LENGTH: 112
<212> TYPE: PRT
<213> ORGANISM: Homo sapiens

<400> SEQUENCE: 16

Gly Pro Val Pro Pro Ser Thr Ala His Leu Glu Leu Ile Glu Glu Leu
1               5                   10                  15

Ile Asn Ile Thr Gln Asn Gln Lys Ala Pro Leu Cys Asn Gly Ser Met
            20                  25                  30

Val Trp Ser Ile Asn Leu Thr Ala Gly Met Tyr Cys Ala Ala Leu Glu
        35                  40                  45

Ser Leu Ile Asn Val Ser Gly Cys Ser Ala Ile Glu Lys Thr Gln Arg
    50                  55                  60

Met Leu Ser Gly Phe Cys Pro His Lys Val Ser Ala Gly Gln Phe Ser
65              70                  75                  80
```

```
Ser Leu His Val Lys Glu Thr Arg Ile Glu Val Ala Gln Phe Val Lys
                85                  90                  95

Asp Leu Leu Asn His Leu Lys Thr Leu Phe Lys Glu Gly Gln Phe Asn
            100                 105                 110

<210> SEQ ID NO 17
<211> LENGTH: 113
<212> TYPE: PRT
<213> ORGANISM: Homo sapiens

<400> SEQUENCE: 17

Pro Gly Pro Val Pro Pro Ser Thr Ala His Leu Glu Leu Ile Glu Glu
  1               5                  10                  15

Leu Ile Asn Ile Thr Gln Asn Gln Lys Ala Pro Leu Cys Asn Gly Ser
                20                  25                  30

Met Val Trp Ser Ile Asn Pro Thr Ala Gly Met Tyr Cys Ala Ala Leu
            35                  40                  45

Glu Ser Leu Ile Asn Val Ser Gly Cys Ser Ala Ile Glu Lys Thr Gln
 50                  55                  60

Arg Met Leu Ser Gly Phe Cys Pro His Lys Val Ser Ala Gly Gln Phe
 65                  70                  75                  80

Ser Ser Leu His Val Met Asp Thr Arg Ile Glu Val Ala Gln Phe Val
                85                  90                  95

Lys Asp Leu Leu Leu His Leu Lys Lys Leu Phe Lys Glu Gly Gln Phe
            100                 105                 110

Asn

<210> SEQ ID NO 18
<211> LENGTH: 113
<212> TYPE: PRT
<213> ORGANISM: Homo sapiens

<400> SEQUENCE: 18

Pro Gly Pro Val Pro Pro Ser Thr Ala His Arg Glu Leu Ile Glu Glu
  1               5                  10                  15

Leu Val Asn Ile Thr Gln Asn Gln Lys Ala Pro Leu Cys Asn Gly Ser
                20                  25                  30

Met Val Trp Ser Ile Asn Leu Thr Ala Gly Met Tyr Cys Ala Ala Leu
            35                  40                  45

Glu Ser Leu Ile Asn Val Ser Gly Cys Ser Ala Ile Glu Lys Thr Gln
 50                  55                  60

Arg Met Leu Ser Gly Phe Cys Pro His Lys Val Ser Ala Gly Gln Phe
 65                  70                  75                  80

Ser Ser Leu His Val Thr Gly Arg Lys Ile Glu Val Ala Gln Phe Val
                85                  90                  95

Lys Asp Leu Leu Leu His Leu Lys Lys Leu Phe Lys Glu Gly Gln Phe
            100                 105                 110

Asn

<210> SEQ ID NO 19
<211> LENGTH: 113
<212> TYPE: PRT
<213> ORGANISM: Homo sapiens
```

-continued

```
<400> SEQUENCE: 19

Pro Gly Pro Val Pro Pro Ser Thr Ala His Arg Glu Leu Ile Glu Glu
 1               5                  10                  15

Leu Val Asn Ile Thr Gln Asn Gln Lys Ala Pro Leu Cys Asn Gly Ser
            20                  25                  30

Met Val Trp Arg Ile Asn Arg Thr Ala Gly Met Tyr Cys Ala Ala Leu
        35                  40                  45

Glu Ser Leu Ile Asn Val Ser Gly Cys Ser Ala Ile Glu Lys Thr Gln
    50                  55                  60

Arg Met Leu Ser Gly Phe Cys Pro His Lys Val Ser Ala Gly Gln Phe
65                  70                  75                  80

Ser Ser Leu His Val Met Asp Ser Arg Ile Glu Val Ala Gln Phe Val
                85                  90                  95

Lys Asp Leu Leu Asn His Leu Arg Ala Leu Phe Lys Glu Gly Gln Phe
            100                 105                 110

Asn

<210> SEQ ID NO 20
<211> LENGTH: 113
<212> TYPE: PRT
<213> ORGANISM: Homo sapiens

<400> SEQUENCE: 20

Pro Gly Pro Val Pro Pro Ser Thr Ala Ala Arg Glu Leu Ile Glu Glu
 1               5                  10                  15

Leu Phe Asn Ile Thr Gln Asn Gln Lys Ala Pro Leu Cys Asn Gly Ser
            20                  25                  30

Met Val Trp Ser Ile Asn Leu Thr Ala Gly Met Tyr Cys Ala Ala Leu
        35                  40                  45

Glu Ser Leu Ile Asn Val Ser Gly Cys Ser Ala Ile Glu Lys Thr Lys
    50                  55                  60

Arg Met Leu Ser Gly Phe Cys Pro His Lys Val Ser Ala Gly Gln Phe
65                  70                  75                  80

Pro Ser Leu His Val Lys Lys Thr Arg Ile Glu Val Ala Gln Phe Val
                85                  90                  95

Lys Asp Leu Leu Ile His Leu Arg Lys Leu Phe Lys Glu Gly Gln Phe
            100                 105                 110

Asn
```

MODIFIED IL-13 POLYPEPTIDES

BACKGROUND

Figure 1:
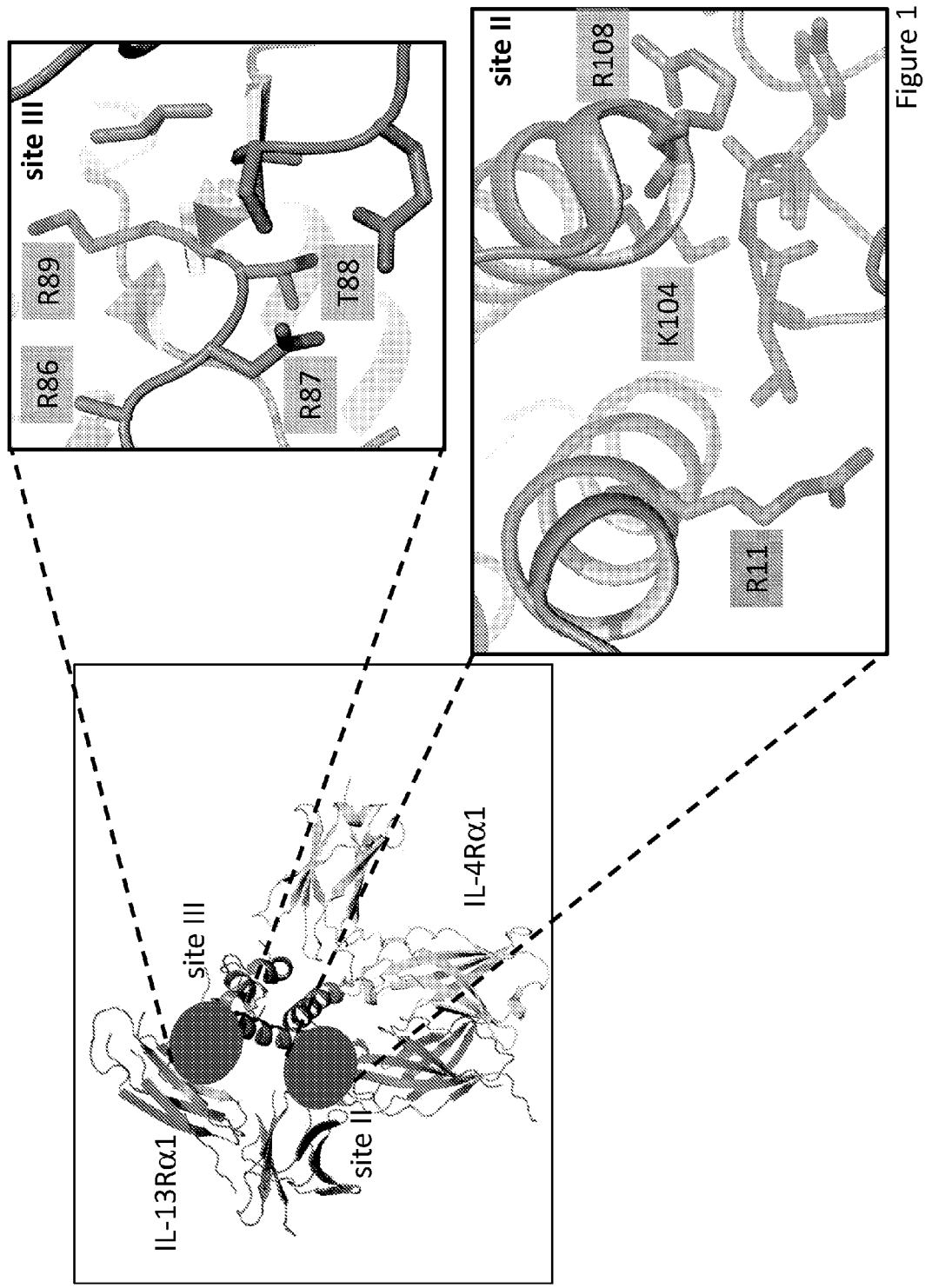

Interleukin-13 (IL-13) is a cytokine secreted by T lymphocytes and mast cells, which shares several biological activities with IL-4, as a mediator of allergic inflammation and disease. IL-13 is involved in the allergic response via its actions on epithelial and smooth muscle cells. IL-13 induces many features of allergic lung disease, including airway hyperresponsiveness, goblet cell metaplasia and mucus hypersecretion, which all contribute to airway obstruction. IL-13 also induces secretion of chemokines that are required for recruitment of allergic effector cells to the lung. Many polymorphisms in the IL-13 gene have been shown to confer an enhanced risk of atopic respiratory diseases such as asthma.

The art has shown that neutralization of endogenously released IL-13 with a soluble form of IL-13Rα2, which binds IL-13 but not IL-4, during antigen exposure largely inhibited the characteristics of asthma in murine asthma models. In addition, antigen challenge of IL-13-deficient mice failed to elicit airway hyperresponsiveness and mucus production despite the continued presence of IL-4 and IL-5 and airway inflammation. Its importance as an effector molecule in asthma was further evidenced by the finding that acute administration of IL-13 itself was sufficient to recapitulate many features of airway responses characterized in asthma, such as eosinophilic inflammation, mucus hyperproduction and airway hyperresponsiveness in mice. It has been suggested that IL-13, independent from other Th2 cytokines, is necessary and sufficient to induce key features of allergic inflammation at an effector phase.

Various biologicals have been tested for treatment of asthma, including humanized monoclonal antibodies (MoAbs) against IL-5 and IL-13, and a recombinant human soluble IL-4 receptor (sIL-4R). For example, to evaluate the biologic and clinical relevance of interleukin-13 in patients with uncontrolled asthma, lebrikizumab, an IgG4 humanized monoclonal antibody that specifically binds to interleukin-13 and inhibits its function was administered. Treatment with lebrikizumab was associated with a significant improvement in prebronchodilator $FEV_1$, the primary outcome.

An important factor in IL-13 biology is the nature of its receptor interactions. Its diverse functions are mediated by a complex receptor system including IL-4 receptor α (IL-4Rα; CD124) and two other cognate cell surface proteins, IL-13Rα1 (CD213a1) and IL-13Rα2 (CD213a2). IL-13Rα1 forms a heterodimer with IL-4Rα that is a signaling IL-13 receptor. In contrast, IL-13Rα2 has been thought to be a decoy receptor due to its short cytoplasmic tail. IL-13Rα2 exists on the cell membrane, intracellularly, and in soluble form. Recent reports revealed that membrane IL-13Rα2 may have some signaling capabilities, and soluble IL-13Rα2 may be an endogenous modulator for IL-13 responses. IL-13Rα2 has an extremely high affinity for IL-13, and can actually out-compete antibodies for IL-13 binding. The other receptor, IL-13Rα1, has a much lower affinity, but is associated with signaling events mediated by IL-4Rα. It induces its effects through a multi-subunit receptor that includes the alpha chain of the IL-4 receptor (IL-4Rα) and IL-13Rα1. Most of the biological effects of IL-13, like those of IL-4, are linked to a single transcription factor, signal transducer and activator of transcription 6 (STAT6).

Biologicals that provide for selective alteration of IL-13 activity are of interest for a number of therapeutic purposes, including the treatment of asthma and atopy, and certain cancers. The present invention addresses this issue.

SUMMARY OF THE INVENTION

IL-13 polypeptides and analogs thereof are provided, which polypeptides provide for selective binding to IL-13 receptors. Certain of the polypeptides of the invention are highly selective antagonists of native IL-13 activity. Other peptides are selective agonists of native IL-13 activity.

The IL-13 polypeptides of the invention are engineered to have one or more of the following properties: (a) altered affinity for IL-13Rα2, relative to the native human IL-13 protein. Such peptides may have decreased affinity, which polypeptides may be designated herein as ($R2^{lo}$); or alternatively may have increased affinity, which polypeptides may be designated herein as ($R2^{+}$); (b) altered affinity for IL-13Rα1 relative to the native human IL-13 protein. Such peptides may have decreased affinity, which polypeptides may be designated herein as ($R1^{lo}$); or alternatively may have increased affinity, which polypeptides may be designated herein as ($R1^{hi}$); (c) a disruption in the binding site for IL-4Rα relative to the native human IL-13 protein, which polypeptides may be referred to herein as ($4R^{null}$).

In some embodiments, amino acid modifications are made at one or more of the amino acids within the set of contact residues that interact with IL-13Rα1, IL-13Rα2 or IL-4Rα1, which residues include, without limitation, L10, R11, I14, E12, V18, R65, R86, D87, T88, K89, L101, K104, K105, F107, and R108 (for reference purposes the sequence of wild-type human IL-13 is provided herein as SEQ ID NO:1, to which the numbering of amino acids will refer). In other embodiments, modified residues are at two or more, three or more, four or more, five or more, and not more than 14 amino acids within the combined set of contact residues defined above.

The IL-13 interface that contacts IL-13Rα1 and IL-13Rα2 is the same, and thus there can be overlap in the altered residues that control affinity for these two receptors. In some embodiments one or more of the native amino acid residues L10, R11, I14, V18, R86, D87, T88, K89, L101, K104, K105, F107, and R108 is substituted, and provides for an altered affinity for one or both of IL-13Rα1 and IL-13Rα2.

In some embodiments an IL-13 peptide of the invention comprises one or more of the amino acids substitutions: (1) L10F; L10I; L10V; L10A; L10D; L10T; L10H; (2) R11S; R11N; R11H; R11L; R11I; (3) I14L; I14F; I14V; I14M; (4) V18L; V18F; V18I; (5) E12A; (6) R65D; (7) R86K; R86T; R86M; (8) D87E; D87K; D87R; D87G; D87S; (9) T88I; T88K; T88R; (10) K89R; K89T; K89M; (11) L101F; L101I; L101Y; L101H; L101N; (12) K104R; K104T; K104M; (13) K105T; K105A; K105R; K105E; (14) F107L; F107I; F107V; F107M; and (15) R108K; R108T; R108M, which substitutions cause an altered affinity for one or both of IL-13Rα1 and IL-13Rα2. In other embodiments, modified residues are at two or more, three or more, four or more, five or more, and not more than 14 amino acids within the combined set of contact residues defined above.

In some embodiments an IL-13 polypeptide of the invention is an IL-13 agonist. Agonists have increased affinity for one or both of IL-13Rα1 and IL-13Rα2; and may have the properties of being $R1^{hi}R2^{lo}$ or may be $R1^{lo}R2^{+}$. Such variants find use in various methods, including without limitation targeting of cancer cells, induction of apoptosis in IL-13 receptor positive cells; and the like.

In other embodiments an IL-13 polypeptide of the invention is an antagonist of IL-13 signaling. Antagonists may be 4R$^{null}$, and in particular may be R1$^{hi}$R2$^{lo}$4R$^{null}$, which antagonists find use in inhibiting the signaling of endogenous IL-13, e.g. for use in treatment of asthma, atopic disease, and other conditions in which there is undesirable IL-13 activity. Alteration of the native amino acid residues E12 and R65 can be sufficient to ablate binding to IL-4Rα, for example the amino acid substitutions E12A and R65D.

The invention also includes pharmaceutical formulations of IL-13 agonists or antagonists, in combination with a pharmaceutically acceptable excipient. Such formulations may be provided as a unit dose, e.g. a dose effective in inhibition of endogenous IL-13 signaling in an individual, for targeting to IL-13R$^+$ cells, etc. Pharmaceutical formulations also include lyophilized or other preparations of the polypeptides of the invention, which may be reconstituted for use.

In some embodiments, methods for therapeutic treatment of atopic disease, including asthma, are provided. Such methods comprise administering to an individual in need thereof an effective dose of an IL-13 antagonist of the invention, wherein the antagonist reduces the undesirable effects of endogenous IL-13 signaling, which may include, for example, eosinophilic inflammation, mucus hyperproduction and airway hyperresponsiveness. In such methods the administration of the IL-13 antagonist may be localized, e.g. to the lungs, or systemic. In some embodiments an aerosol formulation to the lungs is the mode of administration.

In some embodiments, methods are provided for targeting tumor cells expressing IL-13Rα2, which tumors include, without limitation, glioblastoma cells. In such methods the tumor cells are contacted with an $R1^{lo}R2^{hi}$ agonist, which selectively targets the IL-13Rα2 receptor. The agonist may be conjugated to a markers for imaging, e.g. a fluorophore, radiochemical, enzyme marker, etc.; and may be conjugated to a therapeutic agent, e.g. a cytotoxin, a radioactive element, and the like.

In some embodiments, methods are provided for increasing signaling through IL-13Rα1. In such methods a cell of interest is contacted with an effective dose of an $R1^{hi}R2^{lo}$ agonist, which selectively binds to IL-13Rα1. The dose may be effective to induce apoptosis in the cell of interest. The contacting step may be in vivo, e.g. for therapeutic purposes; or in vitro, e.g. for screening and research purposes.

BRIEF DESCRIPTION OF THE DRAWINGS

FIG. 1. Crystal structure of the IL-13 ternary ectodomain complex. Site II and site III interfaces are indicated with a red circle. Left panels show a zoom in on the interfaces where representative positions mutated in the site II (helix A and D) and site III (C-D loop) are highlighted in orange. IL-13 is in orange, IL-13Rα1 is in purple and IL-4Rα1 is in cyan.

FIG. 2. Comparative analysis of the IL-13Rα1- and the IL-13Rα2-selective IL-13 variants (a) Human IL-13 and IL-13Rα1 and IL-13Rα2 selective variants sequences are given for the indicated residue numbers. Kinetic and affinity parameters were determined by surface plasmon resonance. (b) Histogram representation of the normalized $K_D$ binding affinity values for IL-13Rα1 (purple) and IL-13Rα2 (orange) selective variants. IL-13 wt $K_D$ value was normalized to one and the rest of the values were changed accordingly.

FIG. 3. Signaling activation induced by the IL-13Rα1- and the IL-13Rα2-selective IL-13 variants. (a) The IL-13 responsive cell line A549 was stimulated with doses ranging from 500 nM to 5E-06 nM of the different IL-13 variants for fifteen minutes. Cells were then fixed and permeabilized with 100% cold methanol and stained with antibody against phosphorylated State. The percentage of the MFI value was used to plot the data. (b) A549 cells were stimulated with 500 nM of the IL-13 variants for the indicated times, fixed, permeabilized and stained with phospho-specific Stat antibodies as indicated above and the ratio P-Stat6/P-Stat3 was plotted against time.

FIG. 4. Functional outcomes induced by the IL-13Rα1- and the IL-13Rα2-selective IL-13 variants. (a) Human monocytes were purified from peripheral blood mononuclear cells and cultured with 50 ng/ml GM-CSF alone or with the indicated doses of the different IL-13 variants Cells were analyzed on day 6 with mAbs against HLA-DR, CD86, CD209. Data (mean and SEM) are from 3 donors. (b) TF-1 cells were seeded in a p96 well plate (100.000 cells/well) and stimulated for five days with the indicated doses of the IL-13 variants. Cells were then washed twice with cold PBS and fixed with 4% PFA. The number of cells in each well was determined by flow cytometry. The experiment was repeated three times and the means and SEMs were plotted versus the concentration of cytokine used.

FIG. 5. Crystal structure of the IL-13 ternary ectodomain complex. (a) Site I is highlighted with a red circle. Left panel show a closer look of the site I interface where amino acids mutated in the C helix are colored in orange. IL-13 is in orange, IL-13Rα1 is in purple and IL-4Rα1 is in cyan. (b) Sequences for human IL-13 and IL-13dn are given for the indicated residue numbers. Kinetic and affinity parameters were determined by surface plasmon resonance FIG. 6. Analysis of the IL-13dn efficacy in vitro. (a) The IL-13 responsive cell line THP-1 was stimulated with different doses of IL-13 (pink), IL-13dn (orange) and IL-13 in the presence of 50 nM of IL-13dn (green) for fifteen minutes. Cells were fixed and permeabilized with 100% cold methanol and analyzed for Stat6 phosphorylation using phospho-specific antibodies coupled to Alexa-488 fluorochrome. (b) The macrophage cell line Raw264 stably expressing a Stat6 luciferase reporter was seed in a p96 well plate (100.000 cells/plate) and then stimulated with 10 ng/ml of mouse IL-13 in the presence of the indicated doses of IL-13dn for 48 hr. Cells were lysed with 30 μl of lysis buffer (Promega) and the luciferase activity was measured for 1 sec. (c) Human monocytes were purified from peripheral blood mononuclear cells and cultured with 50 ng/ml GM-CSF alone or with 20 ngr/ml of IL-13 wt in the presence of 2 μg/ml of isotype antibody control, anti-IL4Rα1 antibody or IL-13dn. Cells were analyzed on day 6 with mAbs against CD14, CD86, CD209. Data (mean and SEM) are from 3 donors.

FIG. 7. Analysis of the IL-13dn efficacy in vivo. (a) Schematic flowchart where the doses and times used to test the efficacy of IL-13dn in vivo are indicated. (b) qPCR analysis of the expression levels of the Th2 inflammation markers (Muc5ac, Periostin, Arg1, CHIA, YM1, Fizz1) induced by mouse IL-13 in the presence of the indicated dose of IL-13dn.

DEFINITIONS

In the description that follows, a number of terms conventionally used in the field of cell culture are utilized. In order to provide a clear and consistent understanding of the specification and claims, and the scope to be given to such terms, the following definitions are provided.

The terms "inhibitors," "antagonists" refer to an agent that reduces the effective biological activity of IL-13 present in the system, e.g. an animal, a tissue, an in vitro culture system, etc., for example endogenous IL-13 in an individual, usually by interfering with the interaction between IL-13 and one or more of its receptors. For example, an antagonist of the invention may bind tightly to the IL-13Rα1 receptor, but have low affinity to IL-13Rα2, so that it is not "trapped" by that receptor. Antagonists may also have ablated binding to IL-4Rα, to prevent signaling through that receptor. For development purposes the binding may be performed under experimental conditions, e.g. using isolated proteins as binding partners, using portions of proteins as binding partners, using yeast display of proteins or portions of proteins as binding partners, and the like.

Altered Affinity for IL-13Rα2, Relative to the Native Human IL-13 Protein.

The human interleukin 13 receptor, alpha 2 (IL13RA2) may be referenced with the genetic sequence of Genbank accession number NM_000640. The predicted 380-amino acid protein contains a putative signal sequence, an extracellular region with a fibronectin-like domain and typical cytokine receptor motifs, a transmembrane domain, and a short intracellular tail. Amino acid substitutions that provide for altered Rα2 affinity include without limitation (1) L10H; L10A; (2) R11L; (4) V18I; (7) R86M; R86K; R86T; (8) D87K; D87G; (9) T88S; T88K; (10) K89R; (11) L101N; (12) K104R; (13) K105A; K105E; (14) R108K.

IL13 binds with high affinity to IL13RA1, which induces heterodimerization with IL4R to form a complex, or alternatively, IL13 may bind with even greater affinity to IL13RA2, which fails to induce a signal, indicating that it acts as a decoy receptor. The C-terminal tails of the IL4 and IL13 receptor subunits interact with tyrosine kinases of the Janus kinase family (e.g., JAK1), leading to interaction with STATE, which binds to consensus sequences in the promoters of IL4- and IL13-regulated genes.

Figure 2:
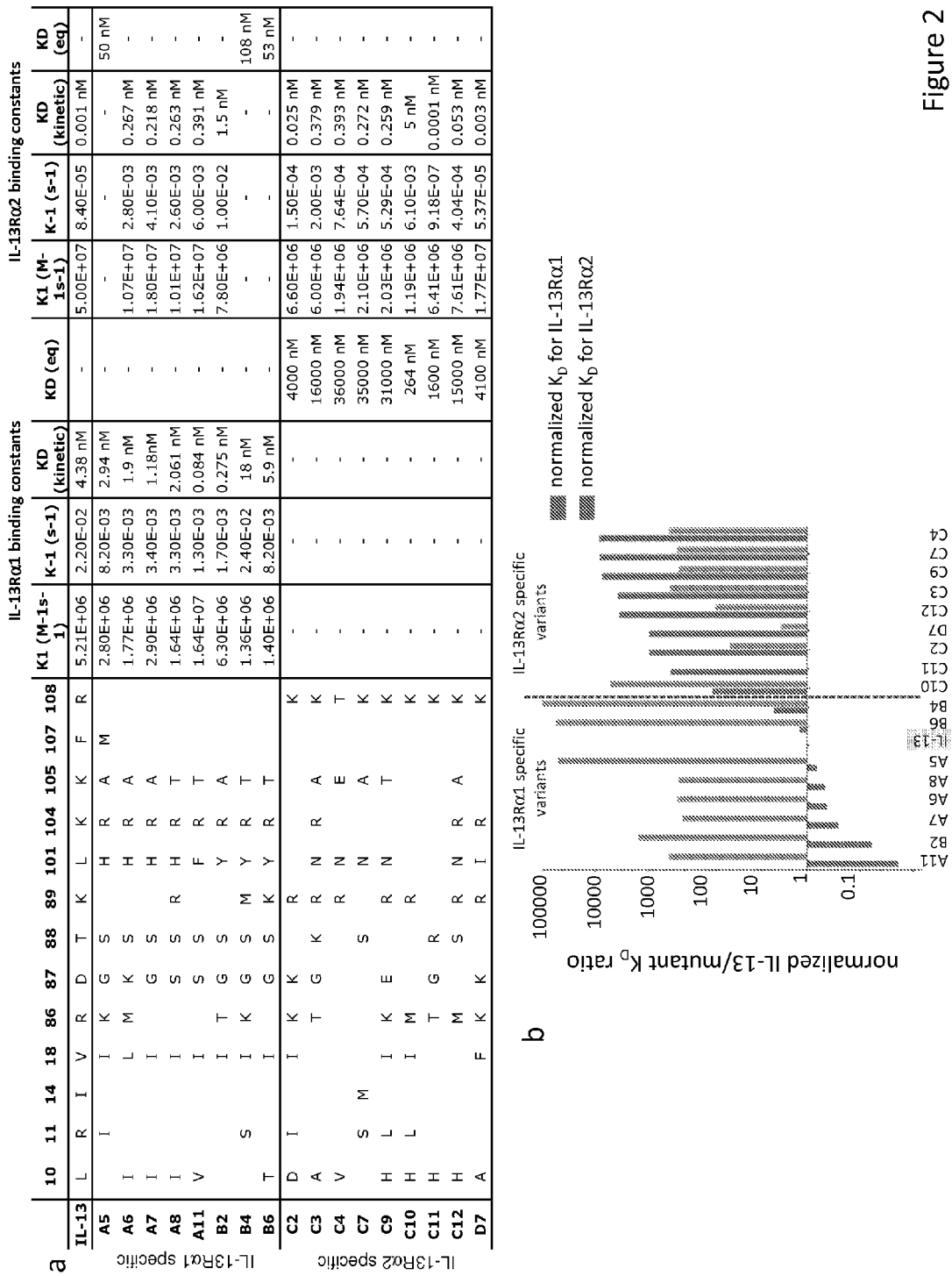
Figure 3:
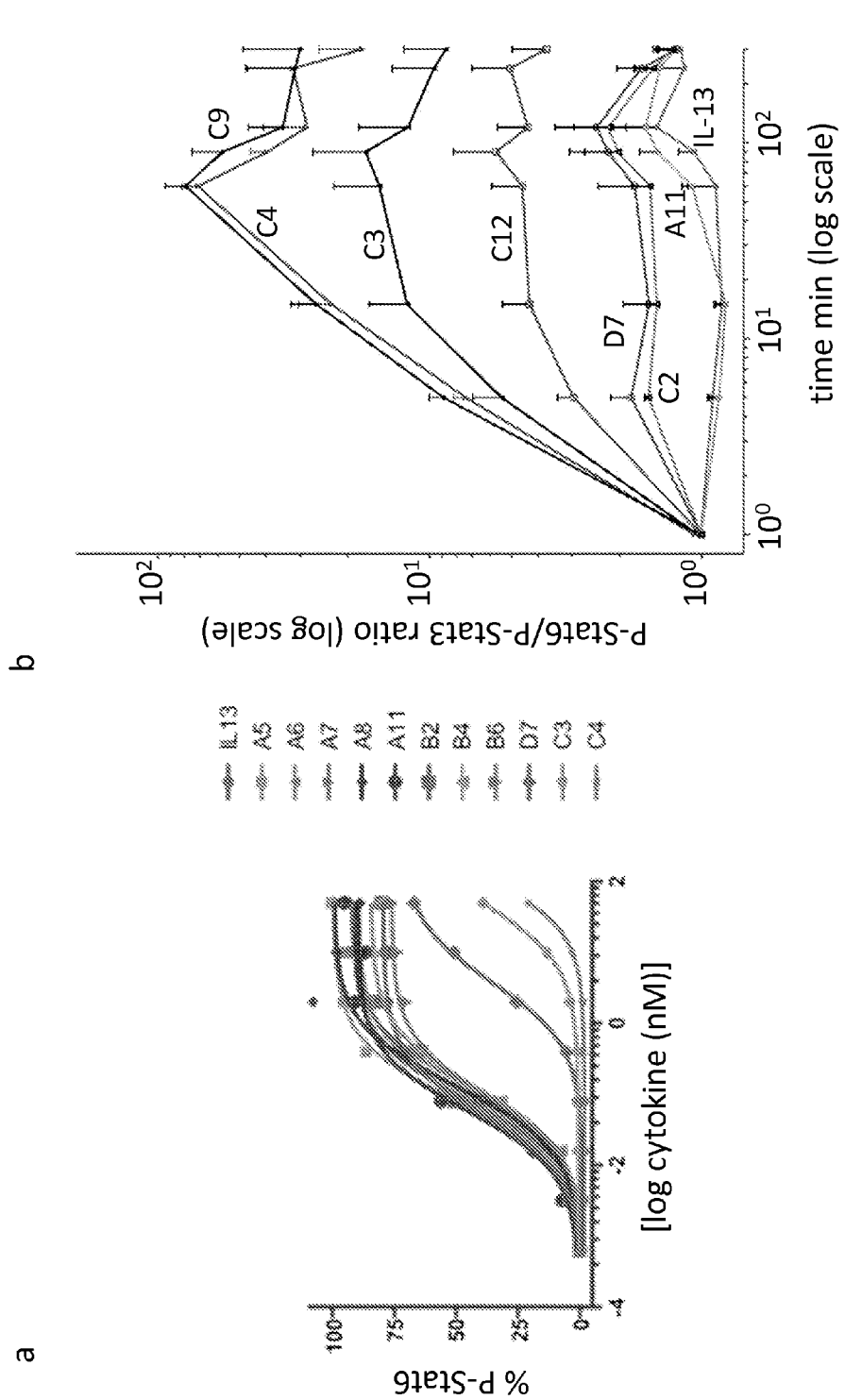
Figure 4:
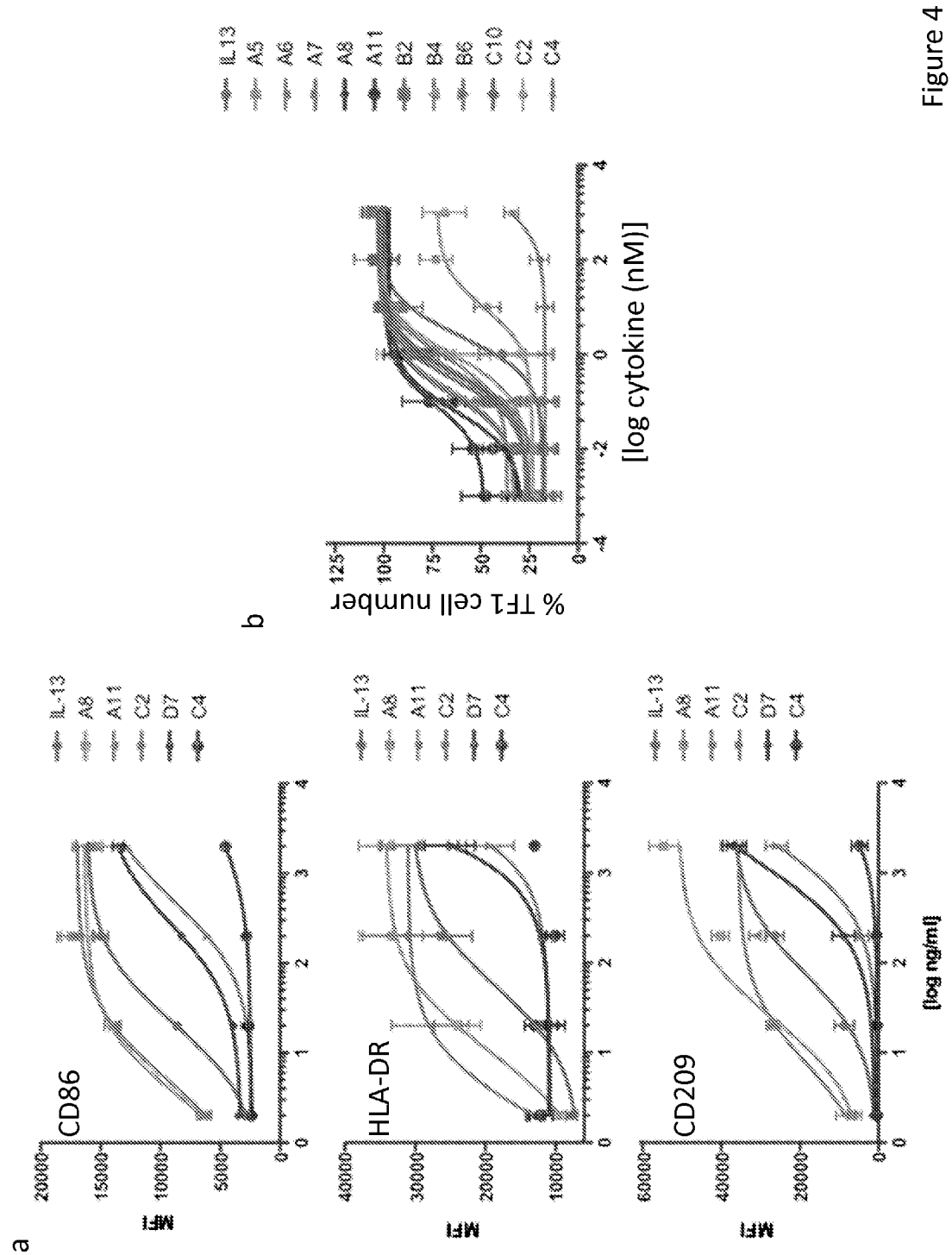
Figure 5:
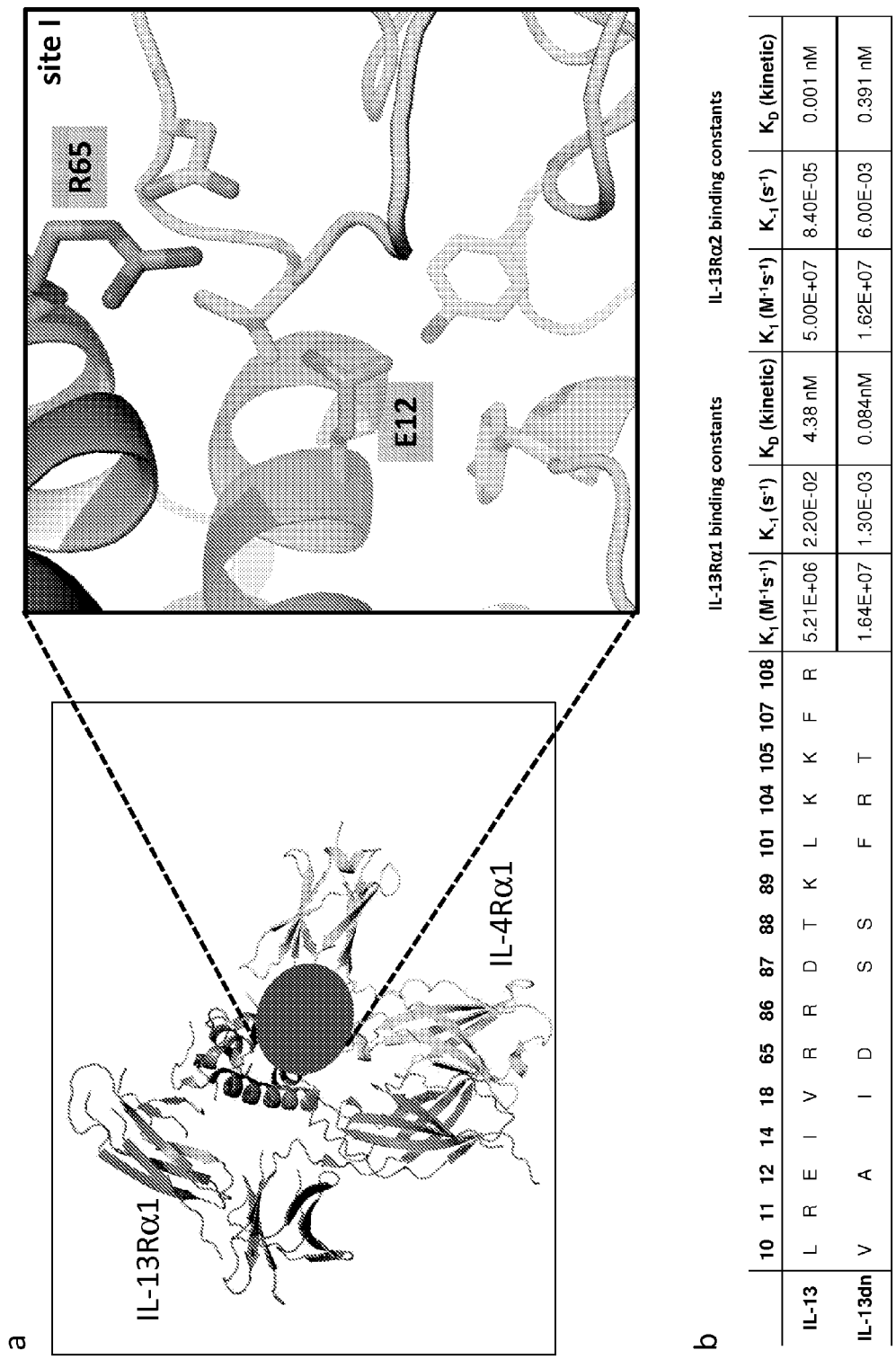
Figure 6:
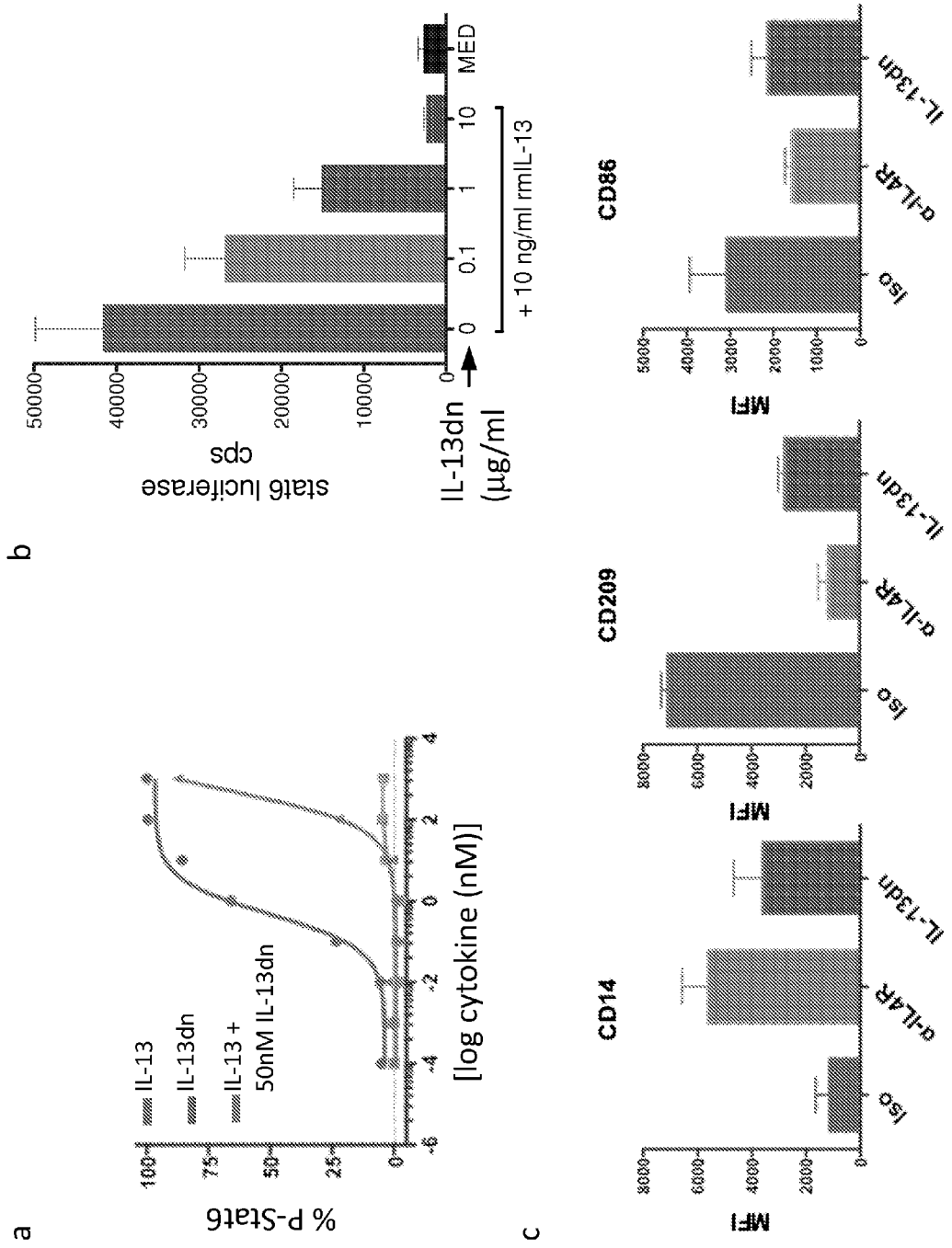
Figure 7:
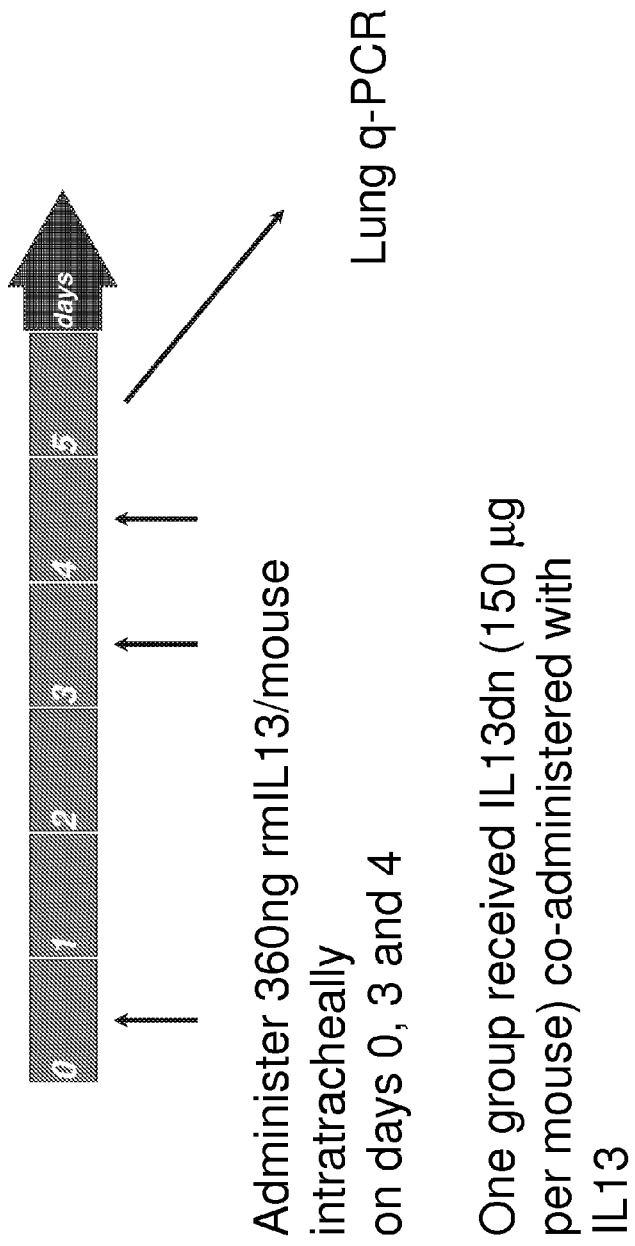
Figure 7:
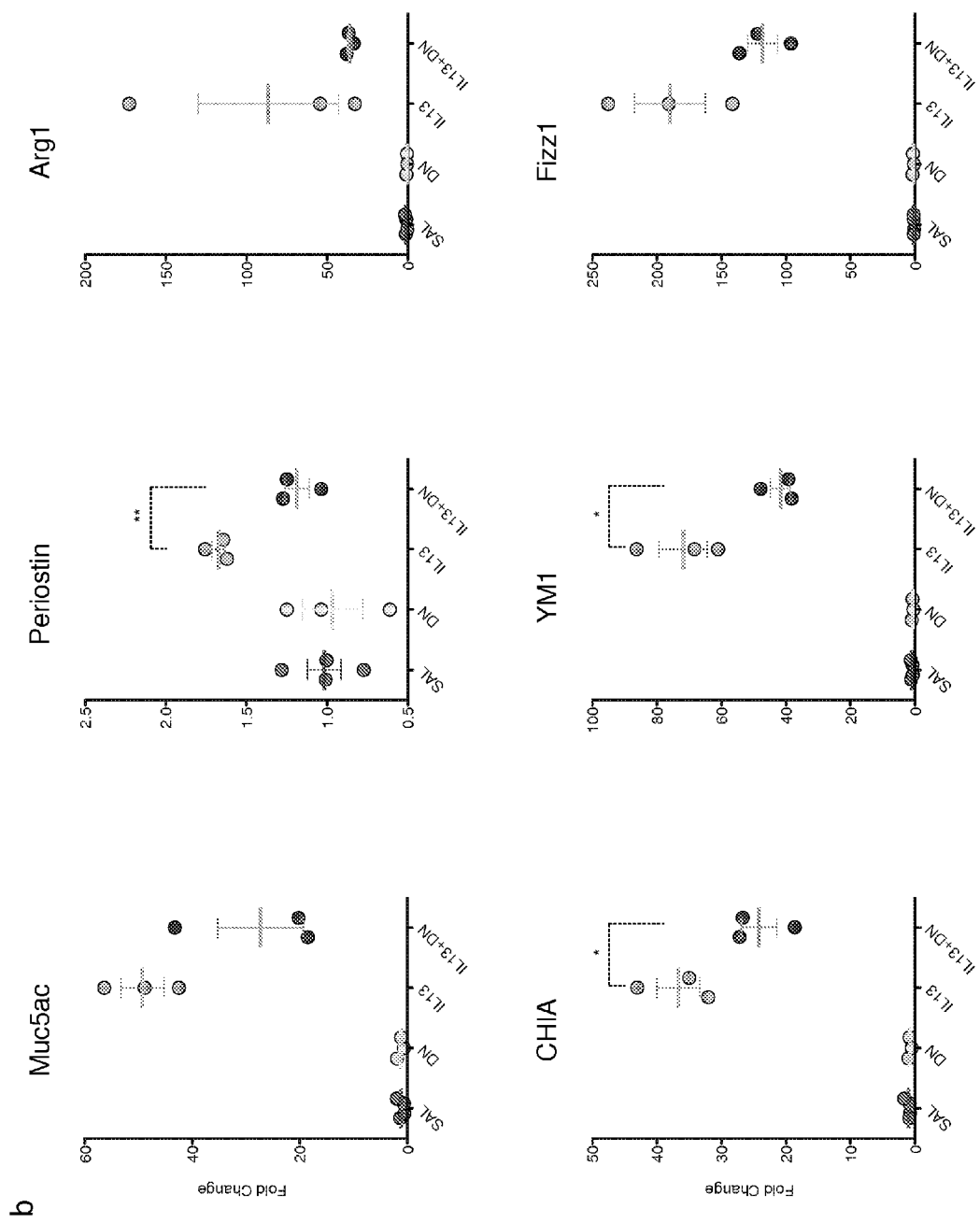

Affinity for IL-13Rα2 to wild-type IL-13 is extremely high, and therefore only modest increases in affinity will be found in polypeptides of the invention, for example equivalent, 2-fold increase, 3-fold increase, 5-fold increase of kinetic $K_D$. With reference to FIG. 2A, peptide C11 (SEQ ID NO:18) and D7 (SEQ ID NO:20) show equivalent or slightly increased binding to IL-13Rα2, and have the set of amino acid substitutions [L10H, R86T, D87G, T88R, R108K] and [L10A, V18F, R86K, D87K, K89R, L101I, K104R, R108K], respectively.

Decreased affinity for IL-13Rα2 is of interest for various purposes, including in particular the design of antagonists. Polypeptides designated as $R2^{lo}$ may have a kinetic $K_D$ that is about 5-fold, about 10-fold, about $10^2$-fold, about $5\times10^2$-fold, about $10^3$-fold lower than a native IL-13 polypeptide. Included in the class is the polypeptide DN (SEQ ID NO:2) [L10V, V18I, D87S, D88S, L101F, K104R, K105T, and in addition the IL-4R binding residues E12A, R65D].

Altered Affinity for IL-13Rα1 Relative to the Native Human IL-13 Protein.

The human interleukin 13 receptor, alpha 1 (IL13RA1) may be referenced with the genetic sequence of Genbank accession number NM_001560. It is a protein of 424 amino acid residues, containing a putative signal sequence and transmembrane domain, which is a low-affinity receptor. Amino acid substitutions that provide for altered Rα1 affinity include without limitation (1) L10I; L10V; (4) V18I; (7) R86K; R86M; (8) D87G; D87S; (9) T88S; (10) K89R; K89M; (11) L101H; L101Y; (12) K104R; (13) K105A; K105T.

Decreases in affinity may be modest, for example equivalent, 2-fold decrease, 3-fold decrease, 5-fold decrease of kinetic $K_D$. Decrease in affinity can also be greater than about 10-fold, greater than about $10^2$-fold, greater than about $10^3$-fold or more. For example, with reference to FIG. 2, polypeptide B4 (SEQ ID NO:9) provides a decreased affinity to IL-13Rα1, and has the set of amino acid substitutions [R11S, V18I, R86K, D87G, T88S, K89M, L101Y, K104R, K105T]. Polypeptide C4 provides a decreased affinity to IL-13Rα1, and has the set of amino acid substitutions [L10V, K89R, L101N, K105E, R108T].

Increased affinity for IL-13α1 is of interest for various embodiments of the invention, in particular when coupled with decreased or equivalent affinity to IL-13Rα2, for example in DN, SEQ ID NO:2. Polypeptides designated as $R1^{hi}$ may have a kinetic $K_D$ that is about 5-fold, about 10-fold, about $10^2$-fold, about $5\times10^2$-fold, about $10^3$-fold higher than a native IL-13 polypeptide. Polypeptides of interest having this property include A11 (SEQ ID NO:4); B2 (SEQ ID NO:8); A5 (SEQ ID NO:5). Sets of amino acid substitutions for A11, B2, and A5, respectively, are as follows: [L10V, V18I, D87S, T88S, L101F, K104R, K105T]; [V18I, R86T, D87G, T88S, L101Y, K104R, K105A]; and [R11I, V18I, R86K, D87G, T88S, L101H, K104R, K105A, F107M].

Disruption in the Binding Site for IL-4Rα Relative to the Native Human IL-13 Protein.

The human interleukin 4, alpha 1 (IL4R) may be referenced with the genetic sequence of Genbank accession number NM_000418. Membrane-bound IL4R is coded by exons 3 to 7 (extracellular domain), exon 9 (transmembrane domain), and exons 10 to 12 (intracellular domain). Alternative splicing leads to the production of a soluble form of IL4R, which is coded by exons 3 to 8 and lacks the exons for the transmembrane and intracellular regions.

Amino acid substitutions at residues E12 and R65 (relative to SEQ ID NO:1) are sufficiently to substantially ablate binding to the IL-4R, which variants may be references as $4R^{null}$. In some embodiments the amino acid substitutions are E12A and R65D, in other embodiments the amino acids are conservative variants thereof, e.g. E12S, E12G, etc.; R65E, and the like.

The binding properties of a binding agent may be measured by any method, e.g., one of the following methods: BIACORE™ analysis, Enzyme Linked Immunosorbent Assay (ELISA), x-ray crystallography, sequence analysis and scanning mutagenesis. The ability of a protein to neutralize and/or inhibit one or more IL-13-associated activities may be measured by the following methods: assays for measuring the proliferation of an IL-13 dependent cell line, e.g. TFI; assays for measuring the expression of IL-13-mediated polypeptides, e.g., flow cytometric analysis of the expression of CD23; assays evaluating the activity of downstream signaling molecules, e.g., STAT6; assays evaluating production of tenascin; assays testing the efficiency of an described herein to prevent asthma in a relevant animal model, e.g., the cynomolgus monkey, and other assays. An IL-13 polypeptide can have a statistically significant effect in one or more of these assays. Exemplary assays for binding properties include the following.

The binding interaction of a IL-13 polypeptide and a target (e.g., receptor) can be analyzed using surface plasmon resonance (SPR). SPR or Biomolecular Interaction Analysis (BIA) detects biospecific interactions in real time, without labeling any of the interactants. Changes in the mass at the binding surface (indicative of a binding event) of the BIA chip result in alterations of the refractive index of light near the surface. The changes in the refractivity generate a detectable signal, which are measured as an indication of real-time reactions between biological molecules. Methods for using SPR are described, for example, in U.S. Pat. No. 5,641,640; Raether (1988) Surface Plasmons Springer Verlag; Sjolander and Urbaniczky (1991) Anal. Chem. 63:2338-2345; Szabo et al. (1995) Curr. Opin. Struct. Biol. 5:699-705 and on-line resources provide by BIAcore International AB (Uppsala, Sweden).

Information from SPR can be used to provide an accurate and quantitative measure of the equilibrium dissociation constant (Kd), and kinetic parameters, including Kon and Koff, for the binding of a molecule to a target. Such data can be used to compare different molecules. Information from SPR can also be used to develop structure-activity relationships (SAR). For example, the kinetic and equilibrium binding parameters of different molecule can be evaluated. Variant amino acids at given positions can be identified that correlate with particular binding parameters, e.g., high affinity and slow Koff. This information can be combined with structural modeling (e.g., using homology modeling, energy minimization, or structure determination by x-ray crystallography or NMR). As a result, an understanding of the physical interaction between the protein and its target can be formulated and used to guide other design processes.

The terms "polypeptide," "peptide" and "protein" are used interchangeably herein to refer to a polymer of amino acid residues. The terms also apply to amino acid polymers in which one or more amino acid residue is an artificial chemical mimetic of a corresponding naturally occurring amino acid, as well as to naturally occurring amino acid polymers and non-naturally occurring amino acid polymer.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, gamma-carboxyglutamate, and O-phosphoserine. Amino acid analogs refers to compounds that have the same basic chemical structure as a naturally occurring amino acid, i.e., an .alpha. carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid.

The term "isolated" refers to a molecule that is substantially free of its natural environment. For instance, an isolated protein is substantially free of cellular material or other proteins from the cell or tissue source from which it is derived. The term refers to preparations where the isolated protein is sufficiently pure to be administered as a therapeutic composition, or at least 70% to 80% (w/w) pure, more preferably, at least 80%-90% (w/w) pure, even more preferably, 90-95% pure; and, most preferably, at least 95%, 96%, 97%, 98%, 99%, or 100% (w/w) pure. A "separated" compound refers to a compound that is removed from at least 90% of at least one component of a sample from which the compound was obtained. Any compound described herein can be provided as an isolated or separated compound.

The terms "subject," "individual," and "patient" are used interchangeably herein to refer to a mammal being assessed for treatment and/or being treated. In an embodiment, the mammal is a human. The terms "subject," "individual," and "patient" encompass, without limitation, individuals having disease. Subjects may be human, but also include other mammals, particularly those mammals useful as laboratory models for human disease, e.g. mouse, rat, etc.

The term "sample" with respect to a patient encompasses blood and other liquid samples of biological origin, solid tissue samples such as a biopsy specimen or tissue cultures or cells derived therefrom and the progeny thereof. The definition also includes samples that have been manipulated in any way after their procurement, such as by treatment with reagents; washed; or enrichment for certain cell populations, such as disease cells. The definition also includes sample that have been enriched for particular types of molecules, e.g., nucleic acids, polypeptides, etc. The term "biological sample" encompasses a clinical sample, and also includes tissue obtained by surgical resection, tissue obtained by biopsy, cells in culture, cell supernatants, cell lysates, tissue samples, organs, bone marrow, blood, plasma, serum, and the like. A "biological sample" includes a sample obtained from a patient's disease cell, e.g., a sample comprising polynucleotides and/or polypeptides that is obtained from a patient's disease cell (e.g., a cell lysate or other cell extract comprising polynucleotides and/or polypeptides); and a sample comprising disease cells from a patient. A biological sample comprising a disease cell from a patient can also include non-diseased cells.

The term "diagnosis" is used herein to refer to the identification of a molecular or pathological state, disease or condition.

The term "prognosis" is used herein to refer to the prediction of the likelihood of death or progression, including recurrence, spread, and drug resistance. The term "prediction" is used herein to refer to the act of foretelling or estimating, based on observation, experience, or scientific reasoning. In one example, a physician may predict the likelihood that a patient will survive.

As used herein, the terms "treatment," "treating," and the like, refer to administering an agent, or carrying out a procedure, for the purposes of obtaining an effect. The effect may be prophylactic in terms of completely or partially preventing a disease or symptom thereof and/or may be therapeutic in terms of effecting a partial or complete cure for a disease and/or symptoms of the disease. "Treatment," as used herein, may include treatment of an atopic disorder or tumor in a mammal, particularly in a human, and includes: (a) preventing the disease or a symptom of a disease from occurring in a subject which may be predisposed to the disease but has not yet been diagnosed as having it (e.g., including diseases that may be associated with or caused by a primary disease; (b) inhibiting the disease, i.e., arresting its development; and (c) relieving the disease, i.e., causing regression of the disease.

Treating may refer to any indicia of success in the treatment or amelioration or prevention of a disease, including any objective or subjective parameter such as abatement; remission; diminishing of symptoms or making the disease condition more tolerable to the patient; slowing in the rate of degeneration or decline; or making the final point of degeneration less debilitating. The treatment or amelioration of symptoms can be based on objective or subjective parameters; including the results of an examination by a physician. Accordingly, the term "treating" includes the administration of the compounds or agents of the present invention to prevent or delay, to alleviate, or to arrest or inhibit development of the symptoms or conditions associated with disease or other diseases. The term "therapeutic effect" refers to the reduction, elimination, or prevention of the disease, symptoms of the disease, or side effects of the disease in the subject.

"In combination with", "combination therapy" and "combination products" refer, in certain embodiments, to the concurrent administration to a patient of a first therapeutic and the compounds as used herein. When administered in combination, each component can be administered at the same time or sequentially in any order at different points in time. Thus, each component can be administered separately but sufficiently closely in time so as to provide the desired therapeutic effect.

"Concomitant administration" of a known disease therapeutic drug with a pharmaceutical composition of the present invention means administration of the drug and IL-13 polypeptide at such time that both the known drug and the composition of the present invention will have a therapeutic effect. Such concomitant administration may involve concurrent (i.e. at the same time), prior, or subsequent administration of the drug with respect to the administration of a compound of the invention. A person of ordinary skill in the art would have no difficulty determining the appropriate timing, sequence and dosages of administration for particular drugs and compositions of the present invention.

Allergy, or Atopy is an increased tendency to IgE-based sensitivity resulting in production of specific IgE antibody to an immunogen, particularly to common environmental allergens such as insect venom, house dust mite, pollens, molds or animal danders. Allergic responses are antigen specific. The immune response to the antigen is further characterized by the over-production of Th2-type cytokines, e.g. IL-4, IL-5 and IL-10, by the responding T cells. The sensitization occurs in genetically predisposed people after exposure to low concentrations of allergen; cigarette smoke and viral infections may assist in the sensitization process.

Included in the group of patients suffering from atopy are those with asthma associated allergies. About 40% of the population is atopic, and about half of this group develop clinical disease ranging from trivial rhinitis to life-threatening asthma. After sensitization, continuing exposure to allergens leads to a significant increase in the prevalence of asthma. Ninety percent of children and 80% of adults with asthma are atopic. Once sensitization has occurred, re-exposure to allergen is a risk factor for exacerbations of asthma. Effective management of allergic asthma includes pharmacological therapy and allergen avoidance. The specific physiological effects of asthma associated allergies include airway inflammation, eosinophilia and mucus production, and antigen-specific IgE and IL-4 production.

Asthma is a respiratory disorder characterized by airway hyperreactivity and inflammation, and is associated with high serum IgE and overproduction of interleukin (IL)-4, IL-5 and IL-13 by allergen-specific Th2 cells.

Cancers of interest include carcinomas, e.g. colon, prostate, breast, melanoma, ductal, endometrial, stomach, dysplastic oral mucosa, invasive oral cancer, non-small cell lung carcinoma, transitional and squamous cell urinary carcinoma, etc.; neurological malignancies, e.g. neuroblastoma, gliomas, etc.; hematological malignancies, e.g. childhood acute leukaemia, non-Hodgkin's lymphomas, chronic lymphocytic leukaemia, malignant cutaneous T-cells, mycosis fungoides, non-MF cutaneous T-cell lymphoma, lymphomatoid papulosis, T-cell rich cutaneous lymphoid hyperplasia, bullous pemphigoid, discoid lupus erythematosus, lichen planus, etc.; sarcomas, melanomas, adenomas; benign lesions such as papillomas, and the like.

The present methods are applicable to brain tumors, particularly glioblastoma. In general, the goals of brain tumor treatments are to remove as many tumor cells as possible, e.g. with surgery, kill as many of the cells left behind after surgery as possible with radiation and/or chemotherapy, and put remaining tumor cells into a nondividing, quiescent state for as long as possible with radiation and chemotherapy. Careful imaging surveillance is a crucial part of medical care, because tumor regrowth requires alteration of current treatment, or, for patients in the observation phase, restarting treatment.

Brain tumors are classified according to the kind of cell from which the tumor seems to originate. Diffuse, fibrillary astrocytomas are the most common type of primary brain tumor in adults. These tumors are divided histopathologically into three grades of malignancy: World Health Organization (WHO) grade II astrocytoma, WHO grade III anaplastic astrocytoma and WHO grade IV glioblastoma multiforme (GBM). WHO grade II astrocytomas are the most indolent of the diffuse astrocytoma spectrum. Astrocytomas display a remarkable tendency to infiltrate the surrounding brain, confounding therapeutic attempts at local control. These invasive abilities are often apparent in low-grade as well as high-grade tumors.

Glioblastoma multiforme is the most malignant stage of astrocytoma, with survival times of less than 2 years for most patients. Histologically, these tumors are characterized by dense cellularity, high proliferation indices, endothelial proliferation and focal necrosis. The highly proliferative nature of these lesions likely results from multiple mitogenic effects. One of the hallmarks of GBM is endothelial proliferation. A host of angiogenic growth factors and their receptors are found in GBMs.

As used herein, the term "correlates," or "correlates with," and like terms, refers to a statistical association between instances of two events, where events include numbers, data sets, and the like. For example, when the events involve numbers, a positive correlation (also referred to herein as a "direct correlation") means that as one increases, the other increases as well. A negative correlation (also referred to herein as an "inverse correlation") means that as one increases, the other decreases.

"Dosage unit" refers to physically discrete units suited as unitary dosages for the particular individual to be treated. Each unit can contain a predetermined quantity of active compound(s) calculated to produce the desired therapeutic effect(s) in association with the required pharmaceutical carrier. The specification for the dosage unit forms can be dictated by (a) the unique characteristics of the active compound(s) and the particular therapeutic effect(s) to be achieved, and (b) the limitations inherent in the art of compounding such active compound(s).

"Pharmaceutically acceptable excipient" means an excipient that is useful in preparing a pharmaceutical composition that is generally safe, non-toxic, and desirable, and includes excipients that are acceptable for veterinary use as well as for human pharmaceutical use. Such excipients can be solid, liquid, semisolid, or, in the case of an aerosol composition, gaseous.

"Pharmaceutically acceptable salts and esters" means salts and esters that are pharmaceutically acceptable and have the desired pharmacological properties. Such salts include salts that can be formed where acidic protons present in the compounds are capable of reacting with inorganic or organic bases. Suitable inorganic salts include those formed with the alkali metals, e.g. sodium and potassium, magnesium, calcium, and aluminum. Suitable organic salts include those formed with organic bases such as the amine bases, e.g., ethanolamine, diethanolamine, triethanolamine, tromethamine, N methylglucamine, and the like. Such salts also include acid addition salts formed with inorganic acids (e.g., hydrochloric and hydrobromic acids) and organic acids (e.g., acetic acid, citric acid, maleic acid, and the alkane- and arene-sulfonic acids such as methanesulfonic acid and benzenesulfonic acid). Pharmaceutically acceptable esters include esters formed from carboxy, sulfonyloxy, and phosphonoxy groups present in the compounds, e.g., $C_{1-6}$ alkyl esters. When there are two acidic groups present, a pharmaceutically acceptable salt or ester can be a mono-acid-mono-salt or ester or a di-salt or ester; and similarly where there are more than two acidic groups present, some or all of such groups can be salified or esterified. Compounds named in this invention can be present in unsalified or unesterified form, or in salified and/or esterified form, and the naming of such compounds is intended to include both the original (unsalified and unesterified) compound and its pharmaceutically acceptable salts and esters. Also, certain compounds named in this invention may be present in more than one stereoisomeric form, and the naming of such compounds is intended to include all single stereoisomers and all mixtures (whether racemic or otherwise) of such stereoisomers.

The terms "pharmaceutically acceptable", "physiologically tolerable" and grammatical variations thereof, as they refer to compositions, carriers, diluents and reagents, are used interchangeably and represent that the materials are capable of administration to or upon a human without the production of undesirable physiological effects to a degree that would prohibit administration of the composition.

A "therapeutically effective amount" means the amount that, when administered to a subject for treating a disease, is sufficient to effect treatment for that disease.

DETAILED DESCRIPTION OF THE EMBODIMENTS

Variant IL-13 polypeptides and analogs thereof are provided. The agents have altered affinity for one or more receptors selected from IL-13Rα1, IL-13Rα2 and IL-4R, as described above in detail. Polypeptides having increased affinity for at least one receptor may find use as agonists for biological activity, and for targeting cells expressing the at least one receptor, e.g. for delivery of therapeutic agents, labeling purposes, and the like. Polypeptides that compete with the native IL-13 protein for binding, and which preferably also are ablated for signaling through the IL-4R find use as antagonists, for example in the treatment of conditions in which there is undesirable IL-13 signaling, such as atopy and asthma.

According to the present invention, amino acid modifications include any naturally occurring or man-made amino acid modifications known or later discovered in the field. In some embodiments, amino acid modifications include any naturally occurring mutation, e.g., substitution, deletion, addition, insertion, etc. In some other embodiments, amino acid modifications include replacing existing amino acid with another amino acid, e.g., a conservative equivalent thereof. In yet some other embodiments, amino acid modifications include replacing one or more existing amino acids with non-natural amino acids or inserting one or more non-natural amino acids. In still some other embodiments, amino acid modifications include at least 1, 2, 3, 4, 5, 6, 8, 10, 12 or 14 amino acid mutations or changes. In some exemplary embodiments, one or more amino acid modifications can be used to alter properties of the IL-13 polypeptide, e.g., affecting the binding activity and/or specificity, etc. Techniques for in vitro mutagenesis of cloned genes are known in the art and described in the Examples herein.

IL-13 polypeptides of the invention may be at least about 50 amino acids in length, at least about 75, at least about 100, at least about 110, at least about 115 amino acids in length, up to the full-length of the wild-type protein at the transmembrane domain, i.e. about 116 amino acids in length, and are optionally fused to a heterologous polypeptide or conjugated to a carrier molecule such as PEG, etc. Exemplary polypeptide sequences are provided in SEQ ID NO:2-SEQ ID NO:20

Sets of modifications may include the following specific changes: (1) L10H; L10A; (2) R11L; (4) V18I; (7) R86M; R86K; R86T; (8) D87K; D87G; (9) T88S; T88K; (10) K89R; (11) L101N; (12) K104R; (13) K105A; K105E; (14) R108K.

Specific sets of modifications may include, without limitation:

[L10H, R86T, D87G, T88R, R108K]
[L10A, V18F, R86K, D87K, K89R, L101I, K104R, R108K],
[L10V, V18I, D87S, D88S, L101F, K104R, K105T]
[R11S, V18I, R86K, D87G, T88S, K89M, L101Y, K104R, K105T]
[L10V, V18I, D87S, T88S, L101F, K104R, K105T]
[L10V, K89R, L101N, K105E, R108T]
[R11S, I14M, T88S, L101N, K105A, R108K]
[L10H, R11L, V18I, R86K, D87E, K89R, L101N, K105T, R108K]
[L10V/I; D87S; T88S; K89R; L101H/F; K104R; K105T]
[L10T/D; R11I; V18I; R86K; D87K/G; T88S; K89R; L101Y; K104R; K105T; R108K]
[L10A/V; R86T; D87G; T88K; K89R; L101N; K104R; K105A/E; R108K/T]
[L10I; V18I; R86T; D87G; T88S; K89R; L101Y/H; K104R; K105A]
[L10V; V18I; D87S; T88S; L101F; K104R; K105T]
[V18I, R86T, D87G, T88S, L101Y, K104R, K105A]
[R11I, V18I, R86K, D87G, T88S, L101H, K104R, K105A, F107M]
[L10V, K89R, L101N, K105E, R108T].

which substitutions are optionally combined with the substitutions [E12A/G/S, R65D/E].

Polypeptide of the present invention can be further modified, e.g., joined to a wide variety of other oligopeptides or proteins for a variety of purposes. For example, post-translationally modified, for example by prenylation, acetylation, amidation, carboxylation, glycosylation, pegylation, etc. Such modifications can also include modifications of glycosylation, e.g. those made by modifying the glycosylation patterns of a polypeptide during its synthesis and processing or in further processing steps; e.g. by exposing the polypeptide to enzymes which affect glycosylation, such as mammalian glycosylating or deglycosylating enzymes.

The ability of a molecule to bind to an IL-13 receptor can be determined, for example, by binding to an IL-13 receptor coated on an assay plate, displayed on a microbial cell surface, in solution, etc. The binding activity of IL-13 variants of the present invention to a receptor can be assayed by immobilizing the receptor or the IL-13 variant to a bead, substrate, cell, etc. Agents can be added in an appropriate buffer and the binding partners incubated for a period of time at a given temperature. After washes to remove unbound material, the bound protein can be released with, for example, SDS, buffers with a high pH, and the like and analyzed.

In some embodiments, a IL-13 variant of the present invention is a fusion protein, e.g., fused in frame with a second polypeptide. In some embodiments, the second polypeptide is capable of increasing the size of the fusion protein, e.g., so that the fusion protein will not be cleared from the circulation rapidly. In some other embodiments, the second polypeptide is part or whole of Fc region. In some other embodiments, the second polypeptide is any suitable polypeptide that is substantially similar to Fc, e.g., providing increased size and/or additional binding or interaction with Ig molecules. These fusion proteins can facilitate purification and show an increased half-life in vivo. Fusion proteins having disulfide-linked dimeric structures (due to the IgG) can also be more efficient in binding and neutralizing other molecules than the monomeric secreted protein or protein fragment alone.

In yet some other embodiments, the second polypeptide is a marker sequence, such as a peptide which facilitates purification of the fused polypeptide. For example, the marker amino acid sequence can be a hexa-histidine peptide, such as the tag provided in a pQE vector (QIAGEN, Inc., 9259 Eton Avenue, Chatsworth, Calif., 91311), among others, many of which are commercially available. As described in Gentz et al., Proc. Natl. Acad. Sci. USA 86: 821-824, 1989, for instance, hexa-histidine provides for convenient purification of the fusion protein. Another peptide tag useful for purification, the "HA" tag, corresponds to an epitope derived from the influenza hemagglutinin protein. Wilson et al., Cell 37: 767, 1984. The addition of peptide moieties to facilitate handling of polypeptides are familiar and routine techniques in the art.

In some other embodiments, IL-13 variants of the present invention include IL-13 variants further modified to improve their resistance to proteolytic degradation or to optimize solubility properties or to render them more suitable as a therapeutic agent. For example, variants of the present invention further include analogs containing residues other than naturally occurring L-amino acids, e.g. D-amino acids or non-naturally occurring synthetic amino acids. D-amino acids may be substituted for some or all of the amino acid residues.

IL-13 variants of the present invention can be produced by any suitable means known or later discovered in the field, e.g., produced from eukaryotic or prokaryotic cells, synthesized in vitro, etc. Where the protein is produced by prokaryotic cells, it may be further processed by unfolding, e.g. heat denaturation, DTT reduction, etc. and may be further refolded, using methods known in the art.

The polypeptides may be prepared by cell-free translation systems, or synthetic in vitro synthesis, using conventional methods as known in the art. Various commercial synthetic apparatuses are available, for example, automated synthesizers by Applied Biosystems, Inc., Foster City, Calif., Beckman, etc. By using synthesizers, naturally occurring amino acids may be substituted with unnatural amino acids. The particular sequence and the manner of preparation will be determined by convenience, economics, purity required, and the like.

The polypeptides may also be isolated and purified in accordance with conventional methods of recombinant synthesis. A lysate may be prepared of the expression host and the lysate purified using HPLC, exclusion chromatography, gel electrophoresis, affinity chromatography, or other purification technique. For the most part, the compositions which are used will comprise at least 20% by weight of the desired product, more usually at least about 75% by weight, preferably at least about 95% by weight, and for therapeutic purposes, usually at least about 99.5% by weight, in relation to contaminants related to the method of preparation of the product and its purification. Usually, the percentages will be based upon total protein.

Methods which are well known to those skilled in the art can be used to construct expression vectors containing coding sequences and appropriate transcriptional/translational control signals. These methods include, for example, in vitro recombinant DNA techniques, synthetic techniques and in vivo recombination/genetic recombination. Alternatively, RNA capable of encoding the polypeptides of interest may be chemically synthesized. One of skill in the art can readily utilize well-known codon usage tables and synthetic methods to provide a suitable coding sequence for any of the polypeptides of the invention. The nucleic acids may be isolated and obtained in substantial purity. Usually, the nucleic acids, either as DNA or RNA, will be obtained substantially free of other naturally-occurring nucleic acid sequences, generally being at least about 50%, usually at least about 90% pure and are typically "recombinant," e.g., flanked by one or more nucleotides with which it is not normally associated on a naturally occurring chromosome. The nucleic acids of the invention can be provided as a linear molecule or within a circular molecule, and can be provided within autonomously replicating molecules (vectors) or within molecules without replication sequences. Expression of the nucleic acids can be regulated by their own or by other regulatory sequences known in the art. The nucleic acids of the invention can be introduced into suitable host cells using a variety of techniques available in the art.

According to the present invention, IL-13 variants can be provided in pharmaceutical compositions suitable for therapeutic use, e.g. for human treatment. In some embodiments, pharmaceutical compositions of the present invention include one or more therapeutic entities of the present invention or pharmaceutically acceptable salts, esters or solvates thereof. In some other embodiments, pharmaceutical compositions of the present invention include one or more therapeutic entities of the present invention in combination with another therapeutic agent, e.g., another anti-tumor agent.

Therapeutic entities of the present invention are often administered as pharmaceutical compositions comprising an active therapeutic agent and a other pharmaceutically acceptable excipient. The preferred form depends on the intended mode of administration and therapeutic application. The compositions can also include, depending on the formulation desired, pharmaceutically-acceptable, non-toxic carriers or diluents, which are defined as vehicles commonly used to formulate pharmaceutical compositions for animal or human administration. The diluent is selected so as not to affect the biological activity of the combination. Examples of such diluents are distilled water, physiological phosphate-buffered saline, Ringer's solutions, dextrose solution, and Hank's solution. In addition, the pharmaceutical composition or formulation may also include other carriers, adjuvants, or nontoxic, nontherapeutic, nonimmunogenic stabilizers and the like.

In still some other embodiments, pharmaceutical compositions of the present invention can also include large, slowly metabolized macromolecules such as proteins, polysaccharides such as chitosan, polylactic acids, polyglycolic acids and copolymers (such as latex functionalized Sepharose™, agarose, cellulose, and the like), polymeric amino acids, amino acid copolymers, and lipid aggregates (such as oil droplets or liposomes).

Methods of Use

According to yet another aspect of the invention, it provides methods for treating, reducing or preventing disease in an individual, including without limitation atopic diseases, by inhibiting the biological activity of IL-13, thereby decreasing IL-13 signaling in the individual. Such methods include administering to a subject in need of treatment a therapeutically effective amount or an effective dose of a high affinity IL-13 polypeptide. Effective doses of the therapeutic entity of the present invention, e.g. for the treatment of disease, vary depending upon many different factors, including means of administration, target site, physiological state of the patient, whether the patient is human or an animal, other medications administered, and whether treatment is prophylactic or therapeutic. Usually, the patient is a human, but nonhuman mammals may also be treated. Treatment dosages need to be titrated to optimize safety and efficacy.

An "IL-13 associated disorder" is one in which IL-13 contributes to a pathology or symptom of the disorder. Accordingly, an IL-13 binding agent, e.g., an IL-13 binding agent that is an antagonist of one or more IL-13 associated activities, can be used to treat or prevent the disorder.

Disorders that can be treated or alleviated by the agents described herein include those respiratory disorders and asthma caused by infectious agents, such as viruses (e.g., cold and flu viruses, respiratory syncytial virus (RSV), paramyxovirus, rhinovirus and influenza viruses. RSV, rhinovirus and influenza virus infections are common in children, and are one leading cause of respiratory tract illnesses in infants and young children. Children with viral bronchiolitis can develop chronic wheezing and asthma, which can be treated using the methods described herein. Also included are the asthma conditions which may be brought about in some asthmatics by exercise and/or cold air. The methods are useful for asthmas associated with smoke exposure (e.g., cigarette-induced and industrial smoke), as well as industrial and occupational exposures, such as smoke, ozone, noxious gases, sulfur dioxide, nitrous oxide, fumes, including isocyanates, from paint, plastics, polyurethanes, varnishes, etc., wood, plant or other organic dusts, etc. The methods are also useful for asthmatic incidents associated with food additives, preservatives or pharmacological agents. Also included are methods for treating, inhibiting or alleviating the types of asthma referred to as silent asthma or cough variant asthma.

The methods disclosed herein are also useful for treatment and alleviation of asthma associated with gastroesophageal reflux (GERD), which can stimulate bronchoconstriction. GERD, along with retained bodily secretions, suppressed cough, and exposure to allergens and irritants in the bedroom can contribute to asthmatic conditions and have been collectively referred to as nighttime asthma or nocturnal asthma. In methods of treatment, inhibition or alleviation of asthma associated with GERD, a pharmaceutically effective amount of the IL-13 polypeptide can be used as described herein in combination with a pharmaceutically effective amount of an agent for treating GERD. These agents include, but are not limited to, proton pump inhibiting agents like PROTONIX® brand of delayed-release pantoprazole sodium tablets, PRILOSEC® brand omeprazole delayed release capsules, ACIPHEX® brand rebeprazole sodium delayed release tablets or PREVACID® brand delayed release lansoprazole capsules.

IL-13 polypeptides can also be useful in treating inflammation and fibrosis, e.g., fibrosis of the liver. IL-13 production has been correlated with the progression of liver inflammation (e.g., viral hepatitis) toward cirrhosis, and possibly, hepatocellular carcinoma (de Lalla et al. (2004) J. Immunol. 173:1417-1425). Fibrosis occurs, e.g., when normal tissue is replaced by scar tissue, often following inflammation. Hepatitis B and hepatitis C viruses both cause a fibrotic reaction in the liver, which can progress to cirrhosis. Cirrhosis, in turn, can evolve into severe complications such as liver failure or hepatocellular carcinoma. Blocking IL-13 activity using the IL-13 polypeptides described herein can reduce inflammation and fibrosis, e.g., the inflammation, fibrosis, and cirrhosis associated with liver diseases, especially hepatitis B and C. For example, an IL-13 polypeptide can be administered in an amount effective to treat or prevent the disorder or to ameliorate at least one symptom of the inflammatory and/or fibrotic disorder.

In another aspect, this application provides compositions, e.g., pharmaceutical compositions, that include a pharmaceutically acceptable carrier and at least one IL-13 polypeptide of the invention.

In another aspect, this application features a method of modulating, e.g., interfering with (e.g., inhibiting, blocking or otherwise reducing), an interaction, e.g., binding, between IL-13 and a cognate IL-13 binding protein, e.g., an IL-13 receptor complex, e.g., a complex comprising IL-13Rα1 and IL-4Rα, or a subunit thereof. The modulating can be effected in vivo or in vitro. In other embodiments, the IL-13 polypeptide of the invention and interferes with (e.g., inhibits, blocks or otherwise reduces) an interaction, e.g., binding, between IL-13 and a subunit of the IL-13 receptor complex, e.g., IL-13Rα1 or IL-4Rα, individually. In yet another embodiment, the IL-13 polypeptide of the invention interferes with (e.g., inhibits, blocks or otherwise reduces) an interaction, e.g., binding, between IL-13 and IL-13Rα1. In another embodiment, the IL-13 polypeptide of the invention interferes with (e.g., inhibits, blocks or otherwise reduces) an interaction, e.g., binding, between IL-13 and IL-13Rα1.

The subject methods can be used on cells in vitro (e.g., in a cell-free system), in culture, e.g. in vitro or ex vivo. For example, IL-13 receptor-expressing cells can be cultured in vitro in culture medium and the contacting step can be effected by adding an IL-13 polypeptide to the culture medium. Alternatively, the method can be performed on cells present in a subject, e.g., as part of an in vivo (e.g., therapeutic or prophylactic) protocol. For example, the IL-13 polypeptide can be delivered locally or systemically.

The method can include contacting IL-13 with the IL-13 receptor complex, or subunit thereof, under conditions that allow an interaction between IL-13 and the IL-13 receptor complex, or subunit thereof, to occur to thereby form an IL-13/IL-13 receptor mixture.

In some embodiments, the dosage may range from about 0.0001 to 100 mg/kg, and more usually 0.01 to 5 mg/kg, of the host body weight. For example dosages can be 1 mg/kg body weight or 10 mg/kg body weight or within the range of 1-10 mg/kg. An exemplary treatment regime entails administration once every two weeks or once a month or once every 3 to 6 months. Therapeutic entities of the present invention are usually administered on multiple occasions. Intervals between single dosages can be weekly, monthly or yearly. Intervals can also be irregular as indicated by measuring blood levels of the therapeutic entity in the patient. Alternatively, therapeutic entities of the present invention can be administered as a sustained release formulation, in which case less frequent administration is required. Dosage and frequency vary depending on the half-life of the polypeptide in the patient.

In prophylactic applications, a relatively low dosage may be administered at relatively infrequent intervals over a long period of time. Some patients continue to receive treatment for the rest of their lives. In other therapeutic applications, a relatively high dosage at relatively short intervals is sometimes required until progression of the disease is reduced or terminated, and preferably until the patient shows partial or complete amelioration of symptoms of disease. Thereafter, the patent can be administered a prophylactic regime.

In still other embodiments, methods of the present invention include treating, reducing or preventing tumor growth, tumor metastasis or tumor invasion of diseases including lymphomas, leukemias, carcinomas, melanomas, glioblastomas, sarcomas, myelomas, etc. For prophylactic applications, pharmaceutical compositions or medicaments are administered to a patient susceptible to, or otherwise at risk of disease in an amount sufficient to eliminate or reduce the risk, lessen the severity, or delay the outset of the disease, including biochemical, histologic and/or behavioral symptoms of the disease, its complications and intermediate pathological phenotypes presenting during development of the disease.

Examples of additional therapeutic agents that can be coadministered and/or coformulated with an IL-13 polypeptide include: inhaled steroids; beta-agonists, e.g., short-acting or long-acting beta-agonists; antagonists of leukotrienes or leukotriene receptors; combination drugs such as ADVAIR®; IgE inhibitors, e.g., anti-IgE antibodies (e.g., XOLAIR®); phosphodiesterase inhibitors (e.g., PDE4 inhibitors); xanthines; anticholinergic drugs; mast cell-stabilizing agents such as cromolyn; IL-4 inhibitors; IL-5 inhibitors; eotaxin/CCR3 inhibitors; and antihistamines. Such combinations can be used to treat asthma and other respiratory disorders. Additional examples of therapeutic agents that can be coadministered and/or coformulated with an IL-13 binding agent include one or more of: TNF antagonists (e.g., a soluble fragment of a TNF receptor, e.g., p55 or p75 human TNF receptor or derivatives thereof, e.g., 75 kd TNFR-IgG (75 kD TNF receptor-IgG fusion protein, ENBREL™)); TNF enzyme antagonists, e.g., TNFα converting enzyme (TACE) inhibitors; muscarinic receptor antagonists; TGF-δ antagonists; interferon gamma; perfenidone; chemotherapeutic agents, e.g., methotrexate, leflunomide, or a sirolimus (rapamycin) or an analog thereof, e.g., CCI-779; COX2 and cPLA2 inhibitors; NSAIDs; immunomodulators; p38 inhibitors, TPL-2, Mk-2 and NFκB inhibitors, among others.

The IL-13 polypeptides of the invention may be used in vitro in binding assays in which they can be utilized in liquid phase or bound to a solid phase carrier. In addition, the polypeptides in these immunoassays can be detectably labeled in various ways. Examples of types of assays which can utilize high affinity IL-13 polypeptides of the invention are flow cytometry, e.g. FACS, MACS, histochemistry, competitive and non-competitive immunoassays in either a direct or indirect format; and the like. Detection of IL-13 receptors using the IL-13 polypeptides of the invention can be done with assays which are run in either the forward, reverse, or simultaneous modes, including histochemical assays on physiological samples. Those of skill in the art will know, or can readily discern, other assay formats without undue experimentation.

The IL-13 polypeptides can be bound to many different carriers and used to detect the presence of IL-13 receptor expressing cells. Examples of well-known carriers include glass, polystyrene, polypropylene, polyethylene, dextran, nylon, amylases, natural and modified celluloses, polyacrylamides, agaroses and magnetite. The nature of the carrier can be either soluble or insoluble for purposes of the invention. Those skilled in the art will know of other suitable carriers for binding proteins, or will be able to ascertain such, using routine experimentation.

There are many different labels and methods of labeling known to those of ordinary skill in the art. Examples of the types of labels which can be used in the present invention include enzymes, radioisotopes, fluorescent compounds, colloidal metals, chemiluminescent compounds, and bioluminescent compounds. Those of ordinary skill in the art will know of other suitable labels for binding to the polypeptides of the invention, or will be able to ascertain such, using routine experimentation. Furthermore, the binding of these labels to the polypeptides of the invention can be done using standard techniques common to those of ordinary skill in the art.

IL-13 receptors may be detected by the IL-13 polypeptides of the invention when present in biological fluids and tissues. A sample can be a liquid such as urine, saliva, cerebrospinal fluid, blood, serum and the like, or a solid or semi-solid such as tissues, feces, and the like, or, alternatively, a solid tissue such as those commonly used in histological diagnosis, for example in tumor tissues.

Another labeling technique which may result in greater sensitivity consists of coupling the polypeptides to low molecular weight haptens. These haptens can then be specifically detected by means of a second reaction. For example, it is common to use haptens such as biotin, which reacts with avidin, or dinitrophenol, pyridoxal, or fluorescein, which can react with specific anti-hapten antibodies.

Compositions for the treatment of disease can be administered by aerosol, parenteral, topical, intravenous, intratumoral, oral, subcutaneous, intraarterial, intracranial, intraperitoneal, intranasal or intramuscular means. A typical route of administration is intravenous or intratumoral, although other routes can be equally effective.

A composition that includes an IL-13 polypeptide of the invention, can be formulated for inhalation or other mode of pulmonary delivery. Accordingly, the IL-13 polypeptide can be administered by inhalation to pulmonary tissue. The term "pulmonary tissue" as used herein refers to any tissue of the respiratory tract and includes both the upper and lower respiratory tract, except where otherwise indicated. An IL-13 polypeptide can be administered in combination with one or more of the existing modalities for treating pulmonary diseases.

In one example the IL-13 polypeptide is formulated for a nebulizer. In one embodiment, the IL-13 polypeptide can be stored in a lyophilized form (e.g., at room temperature) and reconstituted in solution prior to inhalation. It is also possible to formulate the IL-13 polypeptide for inhalation using a medical device, e.g., an inhaler. See, e.g., U.S. Pat. No. 6,102,035 (a powder inhaler) and U.S. Pat. No. 6,012,454 (a dry powder inhaler). The inhaler can include separate compartments for the IL-13 polypeptide at a pH suitable for storage and another compartment for a neutralizing buffer and a mechanism for combining the IL-13 polypeptide with a neutralizing buffer immediately prior to atomization. In one embodiment, the inhaler is a metered dose inhaler.

The three common systems used to deliver drugs locally to the pulmonary air passages include dry powder inhalers (DPIs), metered dose inhalers (MDIs) and nebulizers. MDIs, the most popular method of inhalation administration, may be used to deliver medicaments in a solubilized form or as a dispersion. Typically MDIs comprise a Freon or other relatively high vapor pressure propellant that forces aerosolized medication into the respiratory tract upon activation of the device. Unlike MDIs, DPIs generally rely entirely on the inspiratory efforts of the patient to introduce a medicament in a dry powder form to the lungs. Nebulizers form a medicament aerosol to be inhaled by imparting energy to a liquid solution. Direct pulmonary delivery of drugs during liquid ventilation or pulmonary lavage using a fluorochemical medium has also been explored.

For example, for administration by inhalation, an IL-13 polypeptide is delivered in the form of an aerosol spray from pressured container or dispenser which contains a suitable propellant or a nebulizer. The IL-13 polypeptide may be in the form of a dry particle or as a liquid. Particles that include the IL-13 polypeptide can be prepared, e.g., by spray drying, by drying an aqueous solution of the IL-13 polypeptide with a charge neutralizing agent and then creating particles from the dried powder or by drying an aqueous solution in an organic modifier and then creating particles from the dried powder.

The IL-13 polypeptide may be conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. Capsules and cartridges for use in an inhaler or insufflator may be formulated containing a powder mix of an IL-13 polypeptide and a suitable powder base such as lactose or starch, if the particle is a formulated particle. In addition to the formulated or unformulated compound, other materials such as 100% DPPC or other surfactants can be mixed with the IL-13 polypeptide to promote the delivery and dispersion of formulated or unformulated compound. Methods of preparing dry particles are described, for example, in WO 02/32406.

An IL-13 binding agent, e.g., an anti-IL-13 molecule, can be formulated for aerosol delivery, e.g., as dry aerosol particles, such that when administered it can be rapidly absorbed and can produce a rapid local or systemic therapeutic result. Administration can be tailored to provide detectable activity within 2 minutes, 5 minutes, 1 hour, or 3 hours of administration. In some embodiments, the peak activity can be achieved even more quickly, e.g., within one half hour or even within ten minutes. An IL-13 binding agent, e.g., an anti-IL-13 molecule, can be formulated for longer biological half-life (e.g., by association with a polymer such as PEG) for use as an alternative to other modes of administration, e.g., such that the IL-13 binding agent enters circulation from the lung and is distributed to other organs or to a particular target organ.

Alternatively, compositions are prepared as injectables, either as liquid solutions or suspensions; solid forms suitable for solution in, or suspension in, liquid vehicles prior to injection can also be prepared. The preparation also can be emulsified or encapsulated in liposomes or micro particles such as polylactide, polyglycolide, or copolymer for enhanced adjuvant effect, as discussed above. Langer, Science 249: 1527, 1990 and Hanes, Advanced Drug Delivery Reviews 28: 97-119, 1997. The agents of this invention can be administered in the form of a depot injection or implant preparation which can be formulated in such a manner as to permit a sustained or pulsatile release of the active ingredient. The pharmaceutical compositions are generally formulated as sterile, substantially isotonic and in full compliance with all Good Manufacturing Practice (GMP) regulations of the U.S. Food and Drug Administration.

Toxicity of the proteins described herein can be determined by standard pharmaceutical procedures in cell cultures or experimental animals, e.g., by determining the $LD_{50}$ (the dose lethal to 50% of the population) or the $LD_{100}$ (the dose lethal to 100% of the population). The dose ratio between toxic and therapeutic effect is the therapeutic index. The data obtained from these cell culture assays and animal studies can be used in formulating a dosage range that is not toxic for use in human. The dosage of the proteins described herein lies preferably within a range of circulating concentrations that include the effective dose with little or no toxicity. The dosage can vary within this range depending upon the dosage form employed and the route of administration utilized. The exact formulation, route of administration and dosage can be chosen by the individual physician in view of the patient's condition.

Also within the scope of the invention are kits comprising the compositions of the invention and instructions for use. The kit can further contain a least one additional reagent, e.g. a chemotherapeutic drug, anti-tumor antibody, etc. Kits typically include a label indicating the intended use of the contents of the kit. The term label includes any writing, or recorded material supplied on or with the kit, or which otherwise accompanies the kit.

The invention now being fully described, it will be apparent to one of ordinary skill in the art that various changes and modifications can be made without departing from the spirit or scope of the invention.

EXPERIMENTAL

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

All publications and patent applications cited in this specification are herein incorporated by reference as if each individual publication or patent application were specifically and individually indicated to be incorporated by reference.

The present invention has been described in terms of particular embodiments found or proposed by the present inventor to comprise preferred modes for the practice of the invention. It will be appreciated by those of skill in the art that, in light of the present disclosure, numerous modifications and changes can be made in the particular embodiments exemplified without departing from the intended scope of the invention. For example, due to codon redundancy, changes can be made in the underlying DNA sequence without affecting the protein sequence. Moreover, due to biological functional equivalency considerations, changes can be made in protein structure without affecting the biological action in kind or amount. All such modifications are intended to be included within the scope of the appended claims.

Methods:

Protein expression and purification. Human IL-13 and human IL-13Rα1 and IL-13Rα2-selective variants were cloned into the insect expression vector pAcGP67 (BD Biosciences) with C-terminal 6× Histidine tag and produced in insect Hi5 cells using recombinant baculovirus. Proteins were recovered from Hi5 supernatant after 60 hr of infection by nickel agarose and concentrated and purified by size exclusion chromatography on a Superdex-200 column into HBS (10 mM Hepes pH 7.4, 150 mM NaCl). biotinylated IL-13Rα1 (amino acids 1-310) and IL-4Rα1 (amino acids 1-202) ectodomains were obtained by cloning into the pAcGP67-A vector with a C-terminal biotin acceptor peptide (BAP)-LNDIFEAQKIEWHE and hexahistidine tag. Receptor proteins were coexpressed with BirA ligase with excess biotin (100 μM).

Surface Plasmon Resonance. SPR experiments were conducted on a Biacore T100 instrument. Experiments used a Biacore SA sensor chip (GE Healthcare). Biotinylated IL-13Rα1 and IL-13Rα2 receptors were captured at a low density (100-200 RU) and kinetic runs were conducted at 40 μL/min. An unrelated biotinylated protein was immobilized as a reference surface for the SA sensor chip with matching RU to the experimental surface. All data was analyzed using the Biacore T100 evaluation software version 2.0 with a 1:1 Langmuir binding model. Serial dilutions of unbiotinylated IL-13 variants in the running buffer [1×HBS-P (GE Healthcare)+0.5% BSA] were flowed over the chip and IL-13Rα1/IL-13Rα2 were regenerated by using one 60 second injections of 7 mM glycine (pH 3.0).

Phospho-flow cytometry assay. The IL-13 responsive cell line A549 was stimulated with the indicated doses of IL-13 and IL-13 specific variants for 15 min. Samples were then fixed in PFA for 15 min at room temperature, washed with PBS 0.5% BSA and permeabilized with cold (4° C.) methanol for 10 min. The levels of phosphorylated Stat6 were detected using a maybe anti-pY641 Stat6 coupled to the fluorophore Alexi 488 (BD Bioscience). Analysis was performed on a Becton Dickinson LSRII equipped with 405, 488, and 640 nm lasers. Data analysis was performed in Citibank software. Log median fluorescence intensity values were plotted against cytokine concentration to yield dose-response curves.

TF-1 cells proliferation assay. TF-1 cells were seed to $2\times10^5$ cells/ml in the presence of the indicated doses of IL-13 or the different IL-13 variants for 96 hr. Cells were washed 3× with cold (4C) PBS and fixed with 4% PFA for 15 min at room temperature. Number of cells in each well was determined by flow cytometry. Number of cells were represented as percentage and plotted against cytokine concentration to obtain dose-response curves.

Dendritic cells differentiation assay. $CD14^+$ monocytes were isolated (>97% purity) from peripheral blood mononuclear cells by magnetic separation with anti-CD14 conjugated microbeads (Miltenyi Biotec). $5\times10^5$ $CD14^+$ monocytes were subsequently cultured with 50 ng/mL GM-CSF alone or with the indicated concentrations of IL-13 in the presence of 2 μg/ml of isotype control anti body, anti IL-4Rα1 anti body or IL-13dn in 2 ml well plates containing IMDM medium (Gibco) supplemented with 10% human AB serum, 100 U/mL penicillin, 100 μg/mL streptomycin, 2 mM L-glutamine, sodium pyruvate, non-essential amino acids and 50 μM 2-ME. Cells were processed on day 6 with 5 mM EDTA and subsequently stained with DAPI (Invitrogen), fluorescently labeled isotype control mAbs, or mAbs against CD14, CD86, CD209 and HLA-DR (BD Biosciences). Dendritic cell differentiation was assessed by flow cytometry with a BD LSRII flow cytometer and median fluorescent intensities were generated by FlowJo (Treestar).

In vivo test of IL-13dn efficacy. 360 ng of mouse IL-13 were injected intra-tracheally with or without 150 μg of IL-13dn on days 0, 3 and 5. Lungs were harvest on day six. RNA was extracted and the expression levels of Muc5ac, Periostin, Arg1, CHIA, YM1, Fizz1 were assessed by quantitative PCR.

What is claimed is:

1. A modified IL-13 polypeptide engineered to have decreased affinity for interleukin 13 receptor α2 (IL-13Rα2), relative to native human IL 13 protein; (b) and increased affinity for interleukin 13 receptor α1 (IL-13Rα1) relative to native human IL 13 protein;

wherein the modified IL-13 polypeptide comprises amino acid changes relative to wild type IL-13 at positions V18, D87, T88, L101, K104, and K105.

2. The modified IL-13 polypeptide of claim 1, further comprising amino acid substitutions E12A/G/S and R65D/E wherein the polypeptide is an IL-13R antagonist.

3. The modified IL-13 polypeptide of claim 1, wherein the polypeptide is an IL-13R agonist.

4. The modified IL-13 polypeptide of claim 1, comprising a set of amino acid substitutions selected from

[L10V, V181, D87S, T88S, L101F, K104R, K105T];

[V18I, R86T, D87G, T88S, L101Y, K104R, K105A]; and

[R11I, V181, R86K, D87G, T88S, L101H, K104R, K105A, F107M].

5. The modified IL-13 polypeptide of claim 4, wherein the polypeptide comprises amino acid substitutions E12A/G/S and R65D/E.

6. The modified IL-13 polypeptide of claim 1, comprising an amino acid sequence set forth in any one of SEQ ID NO:2-SEQ ID NO: 10.

7. A therapeutic formulation comprising the polypeptide of claim 1.

* * * * *